(12) United States Patent
Cohen et al.

(10) Patent No.: US 9,445,909 B2
(45) Date of Patent: Sep. 20, 2016

(54) UNICONDYLAR TIBIAL KNEE IMPLANT

(71) Applicant: Mako Surgical Corp., Fort Lauderdale, FL (US)

(72) Inventors: Robert Craig Cohen, Bernardsville, NJ (US); Philip Harris Frank, Maplewood, NJ (US)

(73) Assignee: Mako Surgical Corp., Fort Lauderdale, FL (US)

( * ) Notice: Subject to any disclaimer, the term of this patent is extended or adjusted under 35 U.S.C. 154(b) by 0 days.

(21) Appl. No.: 14/210,921

(22) Filed: Mar. 14, 2014

(65) Prior Publication Data
US 2014/0343681 A1 Nov. 20, 2014

Related U.S. Application Data

(60) Provisional application No. 61/794,339, filed on Mar. 15, 2013.

(51) Int. Cl.
*A61F 2/38* (2006.01)
*A61F 2/30* (2006.01)

(52) U.S. Cl.
CPC ............... *A61F 2/389* (2013.01); *A61F 2/38* (2013.01); *A61F 2/30744* (2013.01); *A61F 2002/30884* (2013.01); *A61F 2002/30967* (2013.01); *A61F 2002/3895* (2013.01)

(58) Field of Classification Search
CPC .......... A61F 2002/30884; A61F 2002/30896; A61F 2/389; A61F 2002/30879; A61F 2002/30901; A61F 2002/30902; A61F 2/38; A61F 2/40; A61F 2002/3895

USPC ............. 623/20.3, 20.32, 19.11–19.14, 623/20.14–20.17, 21.11–21.19, 23.5–23.55, 623/23.72–23.76
See application file for complete search history.

(56) References Cited

U.S. PATENT DOCUMENTS

| | | |
|---|---|---|
| 3,715,763 A | 2/1973 | Link |
| 3,774,244 A | 11/1973 | Walker |
| 3,824,630 A | 7/1974 | Johnston |
| 3,852,830 A | 12/1974 | Marmor |
| 3,958,278 A | 5/1976 | Lee et al. |
| 4,001,896 A | 1/1977 | Arkangel |
| 4,034,418 A | 7/1977 | Jackson et al. |
| 4,085,466 A | 4/1978 | Goodfellow et al. |
| 4,224,696 A | 9/1980 | Murray et al. |

(Continued)

FOREIGN PATENT DOCUMENTS

| | | |
|---|---|---|
| EP | 0611559 A1 | 8/1994 |
| WO | 2011110865 A2 | 9/2011 |

OTHER PUBLICATIONS

International Search Report and Written Opinion for Application No. PCT/US2014/027827 dated Jun. 25, 2014.

(Continued)

*Primary Examiner* — Alvin Stewart
(74) *Attorney, Agent, or Firm* — Lerner, David, Littenberg, Krumholz & Mentlik, LLP

(57) ABSTRACT

An implant providing for both short and long term stability and fixation is disclosed. The implant includes a plurality of projections extending from a bone contacting surface, and a porous material covering at least portions of the surface and projections. The orientation of the projections and the porous material provide for the stability and fixation. Methods of forming and utilizing the implant are also disclosed.

26 Claims, 30 Drawing Sheets

(56) References Cited

U.S. PATENT DOCUMENTS

| | | | |
|---|---|---|---|
| 4,309,778 A | 1/1982 | Buechel et al. | |
| 4,711,639 A | 12/1987 | Grundei | |
| 4,719,908 A | 1/1988 | Averill et al. | |
| 4,743,261 A | 5/1988 | Epinette | |
| 4,795,468 A * | 1/1989 | Hodorek et al. | 623/20.28 |
| 4,935,023 A | 6/1990 | Whiteside et al. | |
| 4,944,757 A * | 7/1990 | Martinez et al. | 623/20.15 |
| 4,978,357 A | 12/1990 | Goymann et al. | |
| 5,037,439 A | 8/1991 | Albrektsson et al. | |
| 5,080,673 A * | 1/1992 | Burkhead | A61F 2/40 623/19.11 |
| 5,080,675 A | 1/1992 | Lawes et al. | |
| 5,152,797 A * | 10/1992 | Luckman et al. | 623/20.16 |
| 5,171,244 A | 12/1992 | Caspari et al. | |
| 5,171,276 A * | 12/1992 | Caspari et al. | 623/16.11 |
| 5,201,881 A | 4/1993 | Evans | |
| 5,203,807 A | 4/1993 | Evans et al. | |
| 5,226,915 A | 7/1993 | Bertin | |
| 5,246,459 A | 9/1993 | Elias | |
| 5,258,032 A | 11/1993 | Bertin | |
| 5,271,737 A * | 12/1993 | Baldwin et al. | 623/20.34 |
| 5,282,866 A | 2/1994 | Cohen et al. | |
| 5,312,411 A | 5/1994 | Steele et al. | |
| 5,314,487 A * | 5/1994 | Schryver et al. | 623/22.37 |
| 5,330,533 A | 7/1994 | Walker et al. | |
| 5,336,266 A | 8/1994 | Caspari et al. | |
| 5,413,604 A | 5/1995 | Hodge | |
| 5,480,444 A | 1/1996 | Incavo et al. | |
| 5,507,820 A | 4/1996 | Pappas | |
| 5,514,183 A | 5/1996 | Epstein et al. | |
| 5,520,695 A | 5/1996 | Luckman | |
| 5,534,027 A | 7/1996 | Hodorek | |
| 5,609,645 A | 3/1997 | Vinciguerra | |
| 5,658,341 A | 8/1997 | Delfosse | |
| 5,716,361 A | 2/1998 | Masini | |
| 5,755,801 A | 5/1998 | Walker et al. | |
| 5,782,925 A | 7/1998 | Collazo et al. | |
| 5,824,103 A | 10/1998 | Williams | |
| 5,871,542 A | 2/1999 | Goodfellow et al. | |
| 5,879,389 A | 3/1999 | Koshino | |
| 5,906,643 A | 5/1999 | Walker | |
| 5,911,758 A | 6/1999 | Oehy et al. | |
| 5,989,261 A | 11/1999 | Walker et al. | |
| 6,059,831 A | 5/2000 | Braslow et al. | |
| 6,068,658 A | 5/2000 | Insall et al. | |
| 6,102,951 A * | 8/2000 | Sutter | A61B 17/17 606/304 |
| 6,102,954 A | 8/2000 | Albrektsson et al. | |
| 6,132,468 A | 10/2000 | Mansmann | |
| 6,152,962 A * | 11/2000 | DeCarlo, Jr. | 623/22.34 |
| 6,179,876 B1 * | 1/2001 | Stamper et al. | 623/18.11 |
| 6,224,632 B1 * | 5/2001 | Pappas et al. | 623/20.34 |
| 6,264,697 B1 | 7/2001 | Walker | |
| 6,342,075 B1 | 1/2002 | MacArthur | |
| 6,344,059 B1 | 2/2002 | Krakovits et al. | |
| 6,379,388 B1 * | 4/2002 | Ensign | A61F 2/389 623/20.21 |
| 6,475,241 B2 | 11/2002 | Pappas | |
| 6,491,726 B2 | 12/2002 | Pappas | |
| 6,494,914 B2 | 12/2002 | Brown et al. | |
| 6,506,216 B1 * | 1/2003 | McCue | A61F 2/389 523/20.14 |
| 6,554,838 B2 | 4/2003 | McGovern et al. | |
| 6,554,866 B1 | 4/2003 | Aicher et al. | |
| 6,558,426 B1 | 5/2003 | Masini | |
| 6,616,696 B1 | 9/2003 | Merchant | |
| 6,620,198 B2 | 9/2003 | Burstein et al. | |
| 6,749,638 B1 | 6/2004 | Saladino | |
| 6,770,097 B2 | 8/2004 | Leclercq | |
| 6,797,006 B2 | 9/2004 | Hodorek | |
| 6,840,960 B2 | 1/2005 | Bubb | |
| 6,890,358 B2 * | 5/2005 | Ball et al. | 623/21.13 |
| 6,916,324 B2 | 7/2005 | Sanford et al. | |
| 6,946,001 B2 | 9/2005 | Sanford et al. | |
| 6,966,928 B2 * | 11/2005 | Fell et al. | 623/14.12 |
| 6,969,393 B2 | 11/2005 | Pinczewski et al. | |
| 7,048,741 B2 | 5/2006 | Swanson | |
| 7,083,652 B2 * | 8/2006 | McCue et al. | 623/20.34 |
| 7,094,241 B2 | 8/2006 | Hodorek et al. | |
| 7,105,027 B2 * | 9/2006 | Lipman et al. | 623/20.29 |
| 7,150,761 B2 | 12/2006 | Justin et al. | |
| 7,258,701 B2 | 8/2007 | Aram et al. | |
| 7,294,149 B2 | 11/2007 | Hozack et al. | |
| 7,357,817 B2 | 4/2008 | D'Alessio, II | |
| 7,465,320 B1 | 12/2008 | Kito et al. | |
| 7,524,334 B2 * | 4/2009 | Haidukewych | 623/20.32 |
| 7,537,664 B2 | 5/2009 | O'Neill et al. | |
| 7,544,210 B2 | 6/2009 | Schaefer et al. | |
| 7,572,293 B2 | 8/2009 | Rhodes et al. | |
| 7,578,850 B2 | 8/2009 | Kuczynski et al. | |
| 7,608,079 B1 | 10/2009 | Blackwell et al. | |
| 7,678,115 B2 | 3/2010 | D'Alessio, II et al. | |
| 7,708,741 B1 | 5/2010 | Bonutti | |
| 7,753,960 B2 | 7/2010 | Cipolletti et al. | |
| 7,842,092 B2 | 11/2010 | Otto et al. | |
| 7,850,698 B2 | 12/2010 | Straszheim-Morley et al. | |
| 7,862,619 B2 * | 1/2011 | Clark | A61F 2/38 623/20.3 |
| 7,896,923 B2 | 3/2011 | Blackwell et al. | |
| 7,896,924 B1 | 3/2011 | Servidio | |
| 7,981,159 B2 | 7/2011 | Williams et al. | |
| 7,998,205 B2 * | 8/2011 | Hagen et al. | 623/14.12 |
| 8,080,063 B2 * | 12/2011 | Ferrand | A61F 2/4081 623/19.11 |
| 8,083,803 B2 | 12/2011 | Albertorio et al. | |
| 8,100,981 B2 | 1/2012 | Clark et al. | |
| 8,114,165 B2 | 2/2012 | Rhodes et al. | |
| 8,137,407 B2 | 3/2012 | Todd et al. | |
| 8,142,510 B2 | 3/2012 | Lee et al. | |
| 8,147,558 B2 * | 4/2012 | Lee et al. | 623/20.3 |
| 8,157,868 B2 | 4/2012 | Walker et al. | |
| 8,163,027 B2 | 4/2012 | Rhodes et al. | |
| 8,187,336 B2 | 5/2012 | Jamali | |
| 8,192,498 B2 | 6/2012 | Wagner et al. | |
| 8,202,323 B2 | 6/2012 | Wyss et al. | |
| 8,211,041 B2 | 7/2012 | Fisher et al. | |
| 8,226,727 B2 * | 7/2012 | Clark et al. | 623/20.36 |
| 8,234,097 B2 * | 7/2012 | Steines et al. | 703/1 |
| 8,236,061 B2 | 8/2012 | Heldreth et al. | |
| 8,273,131 B2 | 9/2012 | Metzger et al. | |
| 8,328,874 B2 | 12/2012 | Lee | |
| 8,337,564 B2 | 12/2012 | Shah et al. | |
| 8,361,147 B2 * | 1/2013 | Shterling et al. | 623/14.12 |
| 8,366,783 B2 | 2/2013 | Samuelson et al. | |
| 8,382,848 B2 | 2/2013 | Ries et al. | |
| 8,403,993 B2 | 3/2013 | Aram et al. | |
| 8,409,293 B1 | 4/2013 | Howard et al. | |
| 8,470,047 B2 | 6/2013 | Hazebrouck et al. | |
| 8,470,048 B2 | 6/2013 | Wolfson et al. | |
| 8,500,816 B2 | 8/2013 | Dees, Jr. et al. | |
| 8,506,571 B2 | 8/2013 | Chana et al. | |
| 8,540,778 B2 * | 9/2013 | Rhodes et al. | 623/20.34 |
| 8,632,600 B2 * | 1/2014 | Zannis et al. | 623/20.17 |
| 8,758,445 B2 * | 6/2014 | Gupta | A61F 2/4261 623/21.11 |
| 8,945,229 B2 * | 2/2015 | Lappin | 623/19.13 |
| 2002/0095214 A1 * | 7/2002 | Hyde, Jr. | 623/18.12 |
| 2002/0173855 A1 | 11/2002 | Mansmann | |
| 2003/0014122 A1 * | 1/2003 | Whiteside | 623/20.32 |
| 2003/0060884 A1 * | 3/2003 | Fell | A61F 2/38 623/14.12 |
| 2003/0100953 A1 * | 5/2003 | Rosa et al. | 623/20.3 |
| 2003/0114933 A1 * | 6/2003 | Bouttens et al. | 623/19.13 |
| 2004/0006393 A1 | 1/2004 | Burkinshaw | |
| 2004/0153087 A1 | 8/2004 | Sanford et al. | |
| 2004/0167630 A1 * | 8/2004 | Rolston | 623/20.14 |
| 2004/0193280 A1 * | 9/2004 | Webster et al. | 623/20.33 |
| 2005/0021145 A1 * | 1/2005 | de Villiers | A61F 2/4425 623/17.14 |
| 2005/0033424 A1 * | 2/2005 | Fell | 623/14.12 |
| 2005/0065611 A1 * | 3/2005 | Huppert | A61F 2/4425 623/17.15 |
| 2005/0112397 A1 * | 5/2005 | Rolfe et al. | 428/593 |
| 2005/0165491 A1 | 7/2005 | Diaz | |

(56) References Cited

U.S. PATENT DOCUMENTS

| | | | |
|---|---|---|---|
| 2005/0169893 A1* | 8/2005 | Koblish et al. | 424/93.7 |
| 2005/0171604 A1 | 8/2005 | Michalow | |
| 2005/0192674 A1 | 9/2005 | Ferree | |
| 2005/0203631 A1 | 9/2005 | Daniels et al. | |
| 2005/0261775 A1* | 11/2005 | Baum et al. | 623/19.12 |
| 2006/0015113 A1 | 1/2006 | Masini | |
| 2006/0064169 A1 | 3/2006 | Ferree | |
| 2006/0129246 A1 | 6/2006 | Steffensmeier | |
| 2006/0147332 A1 | 7/2006 | Jones et al. | |
| 2006/0149387 A1* | 7/2006 | Smith | A61F 2/4081 623/19.11 |
| 2006/0155383 A1* | 7/2006 | Smith et al. | 623/23.51 |
| 2006/0157543 A1* | 7/2006 | Abkowitz et al. | 228/233.2 |
| 2006/0178749 A1 | 8/2006 | Pendleton et al. | |
| 2006/0190086 A1 | 8/2006 | Clemow et al. | |
| 2006/0195196 A1 | 8/2006 | Pendleton et al. | |
| 2006/0200248 A1 | 9/2006 | Beguin et al. | |
| 2006/0217734 A1 | 9/2006 | Sanford et al. | |
| 2006/0235537 A1* | 10/2006 | Kuczynski et al. | 623/20.3 |
| 2006/0235541 A1 | 10/2006 | Hodorek | |
| 2006/0287733 A1 | 12/2006 | Bonutti | |
| 2007/0055269 A1 | 3/2007 | Iannarone et al. | |
| 2007/0067032 A1* | 3/2007 | Felt et al. | 623/14.12 |
| 2007/0083266 A1* | 4/2007 | Lang | 623/17.11 |
| 2007/0100460 A1 | 5/2007 | Rhodes | |
| 2007/0100461 A1 | 5/2007 | Incavo et al. | |
| 2007/0142914 A1 | 6/2007 | Jones et al. | |
| 2007/0173946 A1* | 7/2007 | Bonutti | 623/20.14 |
| 2007/0233269 A1* | 10/2007 | Steines et al. | 623/20.21 |
| 2007/0244564 A1* | 10/2007 | Ferrand | A61F 2/4081 623/19.13 |
| 2007/0255412 A1* | 11/2007 | Hajaj | A61F 2/38 623/17.11 |
| 2007/0299529 A1 | 12/2007 | Rhodes et al. | |
| 2007/0299532 A1* | 12/2007 | Rhodes et al. | 623/20.32 |
| 2008/0027556 A1 | 1/2008 | Metzger | |
| 2008/0027557 A1 | 1/2008 | Tuke | |
| 2008/0058945 A1 | 3/2008 | Hajaj et al. | |
| 2008/0091273 A1* | 4/2008 | Hazebrouck | 623/20.34 |
| 2008/0119938 A1 | 5/2008 | Oh | |
| 2008/0133020 A1* | 6/2008 | Blackwell et al. | 623/20.34 |
| 2008/0139965 A1 | 6/2008 | Meneghini et al. | |
| 2008/0183177 A1* | 7/2008 | Fox et al. | 606/88 |
| 2008/0183291 A1 | 7/2008 | Scheller et al. | |
| 2008/0243259 A1* | 10/2008 | Lee et al. | 623/20.32 |
| 2009/0036984 A1 | 2/2009 | Hagen et al. | |
| 2009/0118830 A1* | 5/2009 | Fell | 623/14.12 |
| 2009/0132047 A1 | 5/2009 | Mansmann et al. | |
| 2009/0138021 A1 | 5/2009 | Colquhoun et al. | |
| 2009/0210066 A1 | 8/2009 | Jasty | |
| 2009/0216325 A1* | 8/2009 | May et al. | 623/11.11 |
| 2009/0226068 A1* | 9/2009 | Fitz et al. | 382/131 |
| 2009/0228114 A1* | 9/2009 | Clark et al. | 623/20.36 |
| 2009/0299481 A9 | 12/2009 | Romagnoli | |
| 2009/0326667 A1 | 12/2009 | Williams et al. | |
| 2010/0016981 A1 | 1/2010 | Roger | |
| 2010/0094429 A1 | 4/2010 | Otto | |
| 2010/0100190 A1 | 4/2010 | May et al. | |
| 2010/0100191 A1* | 4/2010 | May et al. | 623/20.34 |
| 2010/0191341 A1 | 7/2010 | Byrd | |
| 2010/0217395 A1* | 8/2010 | Bertagnoli | A61B 17/14 623/17.16 |
| 2010/0249941 A1* | 9/2010 | Fell | A61F 2/389 623/20.28 |
| 2010/0298947 A1 | 11/2010 | Unger | |
| 2010/0305575 A1 | 12/2010 | Wilkinson et al. | |
| 2010/0312350 A1 | 12/2010 | Bonutti | |
| 2011/0004316 A1 | 1/2011 | Murray et al. | |
| 2011/0015751 A1 | 1/2011 | Laird | |
| 2011/0022179 A1 | 1/2011 | Andriacchi et al. | |
| 2011/0029089 A1* | 2/2011 | Giuliani | A61F 2/40 623/19.14 |
| 2011/0029092 A1 | 2/2011 | Deruntz et al. | |
| 2011/0035018 A1* | 2/2011 | Deffenbaugh et al. | 623/20.28 |
| 2011/0066246 A1* | 3/2011 | Ries et al. | 623/20.27 |
| 2011/0112650 A1 | 5/2011 | Masini | |
| 2011/0178605 A1 | 7/2011 | Auger et al. | |
| 2011/0178606 A1 | 7/2011 | Deffenbaugh et al. | |
| 2011/0178607 A1 | 7/2011 | Oosthuizen | |
| 2011/0184528 A1* | 7/2011 | Beckendorf et al. | 623/23.42 |
| 2011/0190898 A1* | 8/2011 | Lenz et al. | 623/20.32 |
| 2011/0218635 A1 | 9/2011 | Amis et al. | |
| 2012/0016482 A1* | 1/2012 | Mooradian et al. | 623/18.11 |
| 2012/0022658 A1 | 1/2012 | Wentorf | |
| 2012/0041564 A1* | 2/2012 | Landon | A61F 2/389 623/20.34 |
| 2012/0046752 A1 | 2/2012 | Blanchard et al. | |
| 2012/0109324 A1 | 5/2012 | Keggi et al. | |
| 2012/0116524 A1* | 5/2012 | Walker et al. | 623/20.35 |
| 2012/0136452 A1 | 5/2012 | Richter et al. | |
| 2012/0191204 A1 | 7/2012 | Bae et al. | |
| 2012/0209390 A1 | 8/2012 | Gosset et al. | |
| 2012/0245699 A1 | 9/2012 | Lang et al. | |
| 2012/0265315 A1* | 10/2012 | Kusogullari | A61F 2/4003 623/19.14 |
| 2012/0296436 A1* | 11/2012 | Klawitter et al. | 623/19.14 |
| 2012/0310361 A1 | 12/2012 | Zubok et al. | |
| 2012/0330429 A1 | 12/2012 | Axelson, Jr. et al. | |
| 2012/0330431 A1 | 12/2012 | Rolston | |
| 2013/0018477 A1 | 1/2013 | Muratoglu et al. | |
| 2013/0020733 A1* | 1/2013 | Berger | 264/40.1 |
| 2013/0030540 A1 | 1/2013 | Leibinger | |
| 2013/0102929 A1 | 4/2013 | Haight et al. | |
| 2013/0103159 A1 | 4/2013 | Andriacchi et al. | |
| 2013/0144393 A1 | 6/2013 | Mutchler et al. | |
| 2013/0166037 A1* | 6/2013 | Goodfellow et al. | 623/20.32 |
| 2013/0204258 A1 | 8/2013 | Goodfellow et al. | |
| 2013/0204384 A1* | 8/2013 | Hensley et al. | 623/20.35 |
| 2013/0218284 A1* | 8/2013 | Eickmann et al. | 623/20.34 |
| 2014/0128983 A1 | 5/2014 | Flaherty et al. | |
| 2014/0236308 A1* | 8/2014 | Oosthuizen | 623/20.28 |
| 2014/0243990 A1* | 8/2014 | Collazo et al. | 623/20.32 |
| 2014/0277520 A1* | 9/2014 | Chavarria et al. | 623/19.13 |
| 2014/0277528 A1* | 9/2014 | Mines et al. | 623/20.16 |
| 2014/0277539 A1* | 9/2014 | Cook et al. | 623/20.32 |
| 2014/0277548 A1* | 9/2014 | Cohen et al. | 623/20.34 |
| 2014/0296985 A1 | 10/2014 | Balasubramanian et al. | |
| 2014/0324179 A1* | 10/2014 | Salehi et al. | 623/20.32 |
| 2014/0343681 A1* | 11/2014 | Cohen et al. | 623/20.32 |
| 2015/0018956 A1 | 1/2015 | Steinmann et al. | |
| 2015/0134063 A1 | 5/2015 | Steinmann et al. | |

OTHER PUBLICATIONS

Berger et. al. Results of Unicompartmental Knee Arthroplasty at a Minimum of Ten Years of Follow. Journal of Bone and Joint Surgery; May 2005; 87, 5; Proquest Central, p. 999.

Bert et. al. A Comparison of the Mechanical Stability of Various Unicompartmental Tibial. Orthopedics; Jun. 1994; 17, 6; Proquest Central, p. 559.

Bloebaum et. al. Postmortem Analysis of Bone Growth Into Porous-Coated Acetabular Components. Journal of Bone and Joint Surgery; Jul. 1997; 79, 7; Proquest Central p. 1013.

Burton et. al. Computer-Assisted Fluoroguide Navigation of Unicompartmental Knee Arthroplasty. Can J Surg, vol. 52, No. 5, Oct. 2009.

Callaghan et. al. Mobile-Bearing Knee Replacement: Concepts and Results. Journal of Bone and Joint Surgery; Jul. 2000; 82, 7; Proquest Central p. 1020.

Collier et.al. Shelf Age of the Polyethylene Tibial Component and Outcome of Unicondylar Knee. Journal of Bone and Joint Surgery; Apr. 2004; 86, 4; Proquest Central p. 763.

Diezi et al. Effect of Femoral to Tibial Varus Mismatch on the Contact Area of Unicondylar Knee Prostheses. The Knee 17 (2010) 350-355.

Forsythe et. al. Unicondylar Knee Arthroplasty: A Cementless Perspective. Canadian Journal of Surgery; Dec. 2000; 43, 6; Proquest Central p. 417.

Geller et. al. Unicompartmental Knee Arthroplasty: A Controversial History and a Rationale for Contemporary Resurgence. J Knee Surg. 2008; 21:7-14.

(56) References Cited

OTHER PUBLICATIONS

Hall et. al. Unicompartmental Knee Arthroplasty (Alias Uni-Knee): An Overview With Nursing Implications. Orthopaedic Nursing; May/Jun. 2004; 23, 3; Proquest Central,p. 163.

Harman et. al. Polyethylene Insert Damage in Unicondylar Knee Replacement: A comparison of in vivo function and in vitro simulation. A Proceedings of the Institution of Mechanical Engineers; 2010; 224, H7; Proquest Central, p. 823.

Hofmann et. al. Modular Uncemented Tricompartmental Total Knee Arthroplasty. A Comparison Between Posttraumatic and Nonposttraumatic Osteoarthrosis. European Journal of Trauma 2005 No. 2 © Urban & Vogel.

Kasisa et. al. The Precision and Accuracy of Templating the Size of Unicondylar Knee Arthroplasty. The Knee 11 (2004) 395-398.

Lavernia et al. Knee Arthroplasty: Growing Trends and Future Problems. Int. J. Clin. Rheumatol. (2010) 5(5), 565-579.

Lecuire et. al. Mid-Term Results of a New Cementless Hydroxyapatite Coated Anatomic Unicompartmental Knee Arthroplasty. Eur J Orthop Surg Traumatol (2008) 18:279-285. DOI 10.1007/S00590-008-0299-4.

Rosa et. al. An Evaluation of All-Ultra-High Molecular Weight Polyethylene Unicompartmental Tibial Component Cement-Fixation Mechanisms.Journal of Bone and Joint Surgery; 2002; 84, Proquest Central.

Saccomanni et. al. Unicompartmental Knee Arthroplasty: A Review of Literature. Clin Rheumatol (2010) 29:339-346; DOI 10.1007/S10067-009-1354-1.

Sanchis-Alfonso et al. Extensive Osteolytic Cystlike Area Associated With Polyethylene Wear Debris Adjacent to an Aseptic, Stable, Uncemented Unicompartmental Knee Prosthesis: Case Report. Knee Surg, Sports Traumatol, Arthrosc, (2001) 9 :173-177.

Soininvaara et. al. Periprosthetic Bone Mineral Density Changes After Unicondylar Knee Arthroplasty. The Knee 20 (2013) 120-127.

Sorrells et. al. The Clinical History and Development of the Low Contact Stress Total Knee Arthroplasty. Orthopedics; Feb. 2002; 25, 2; Proquest Central p. S207.

Sorrells et. al. The Rotating Platform Mobile Bearing TKA. Orthopedics; Sep. 1996; 19, 9; Proquest Central, p. 793.

Suero et. al. Effects of Tibial Slope Changes in the Stability of Fixed Bearing Medial Unicompartmental Arthroplasty in Anterior Cruciate Ligament Deficient Knees. The Knee 19 (2012) 365-369.

Tanavalee et. al. Unicondylar Knee Arthroplasty: Past and Present. Orthopedics; Dec. 2005; 28, 12; Proquest Central, p. 1423.

Whiteside et al. Effect of Porous-Coating Configuration on Tibial Osteolysis After Total Knee Arthroplasty. Clinical Orthopaedics & Related Research: Dec. 1995.

Epinette et. al.,"Is Hydroxyapatite A Reliable Fixation Option In Unicompartmental Knee Arthroplasty? A 5- To 13-Year Experience With The Hydroxyapatite-Coated Unix Prosthesis", The Journal Of Knee Surgery, Oct. 2008, vol. 21, No. 4, pp. 299-306.

Web Page: "Partial Knee Replacement (Unicondylar Knee Replacement) Program", Downloaded on Jun. 16, 2014, <http://www.hss.edu/condition-list_partial-knee-replacement-conditions.asp>.

* cited by examiner

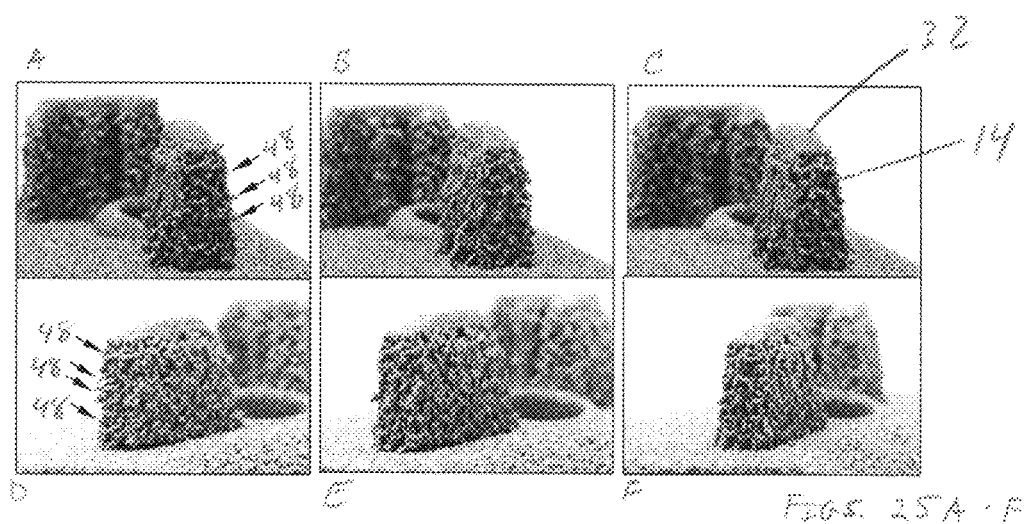
FIGS. 25A-F
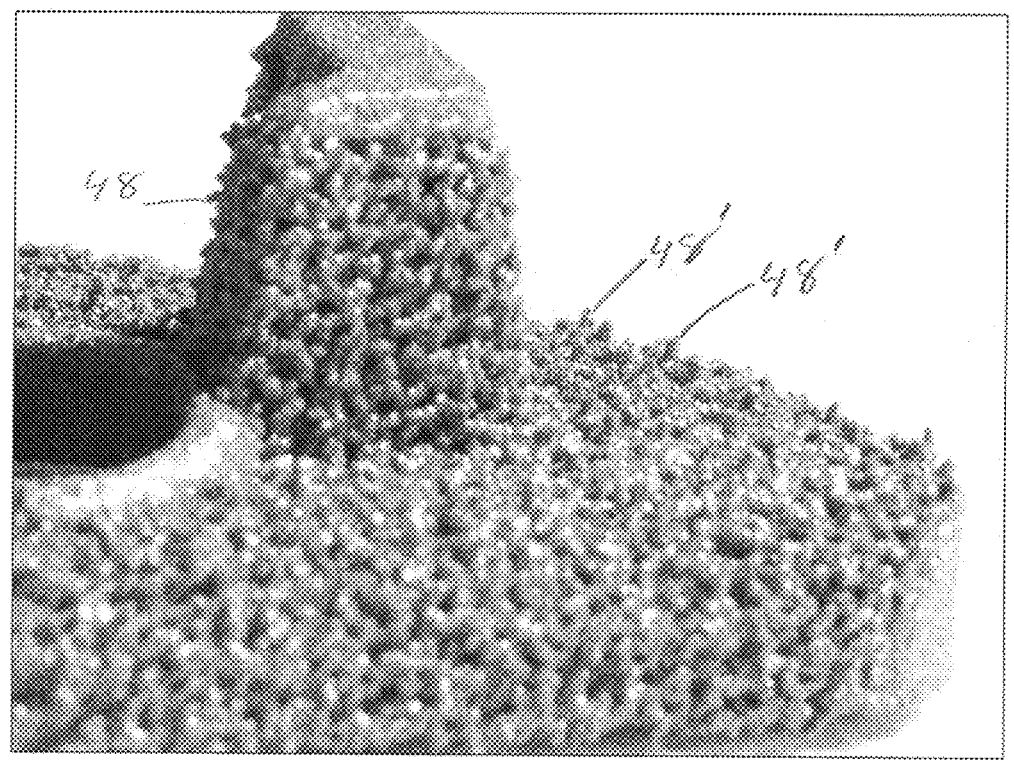
FIG. 26

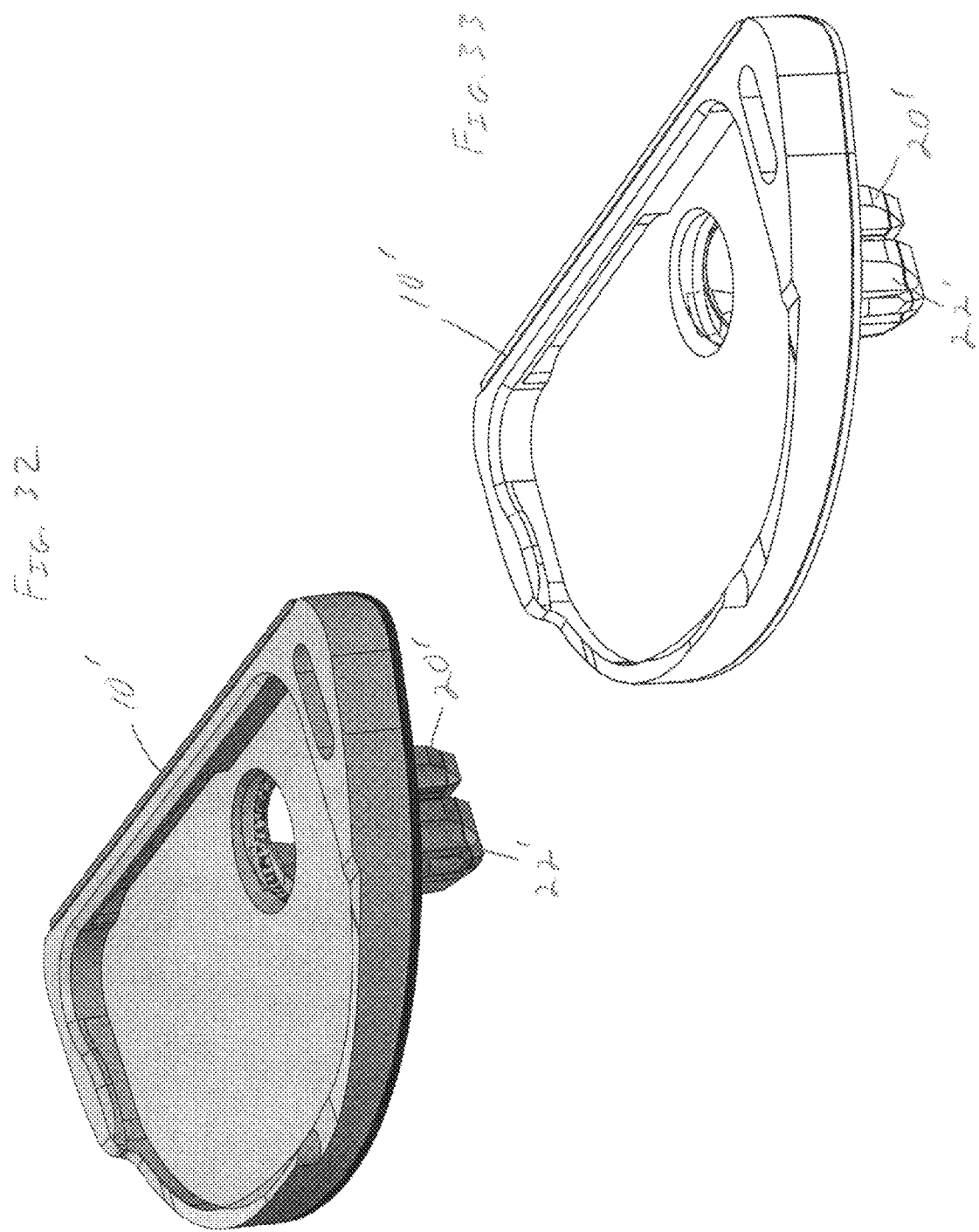

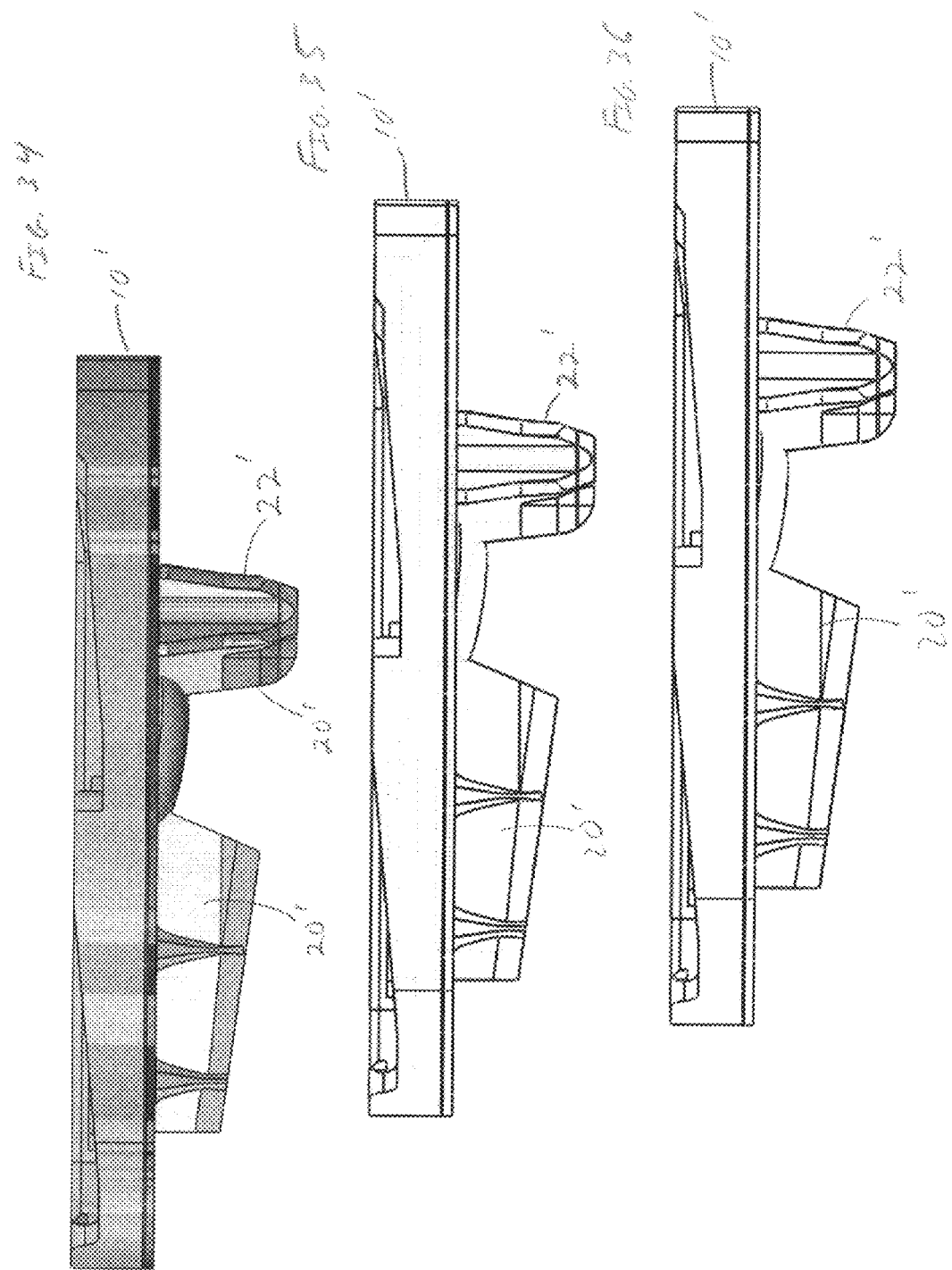

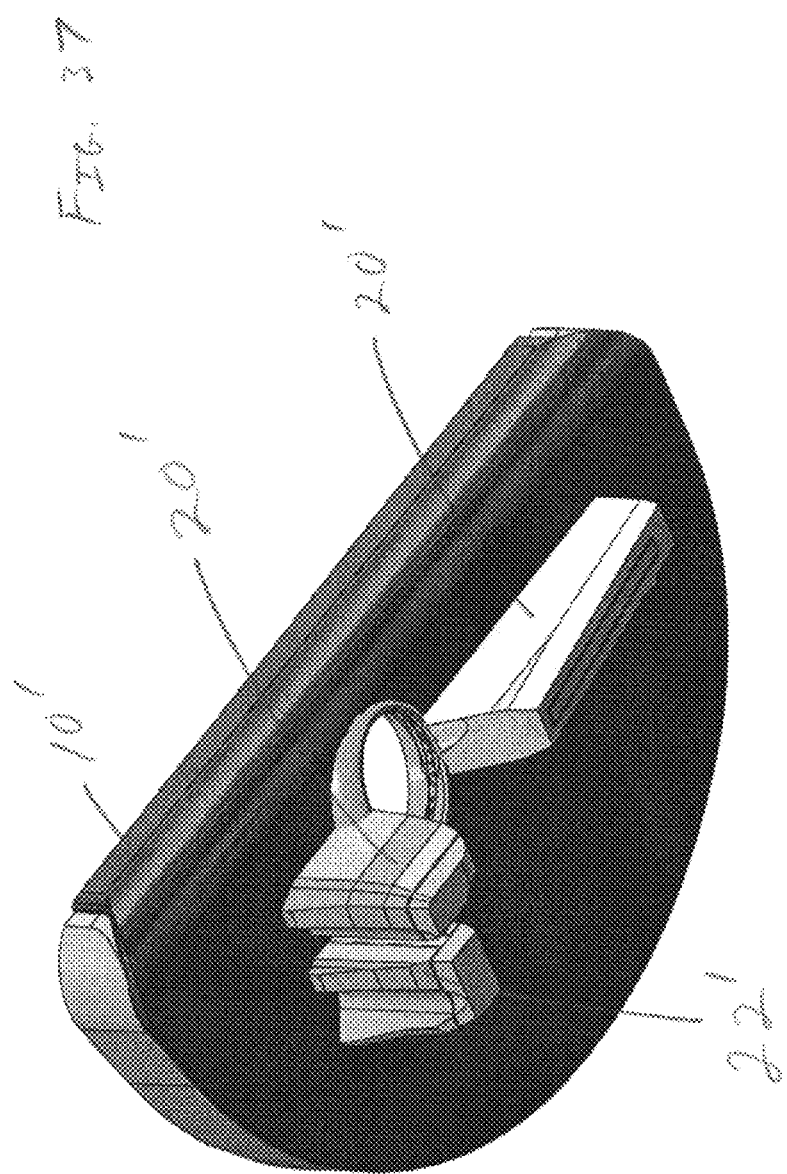

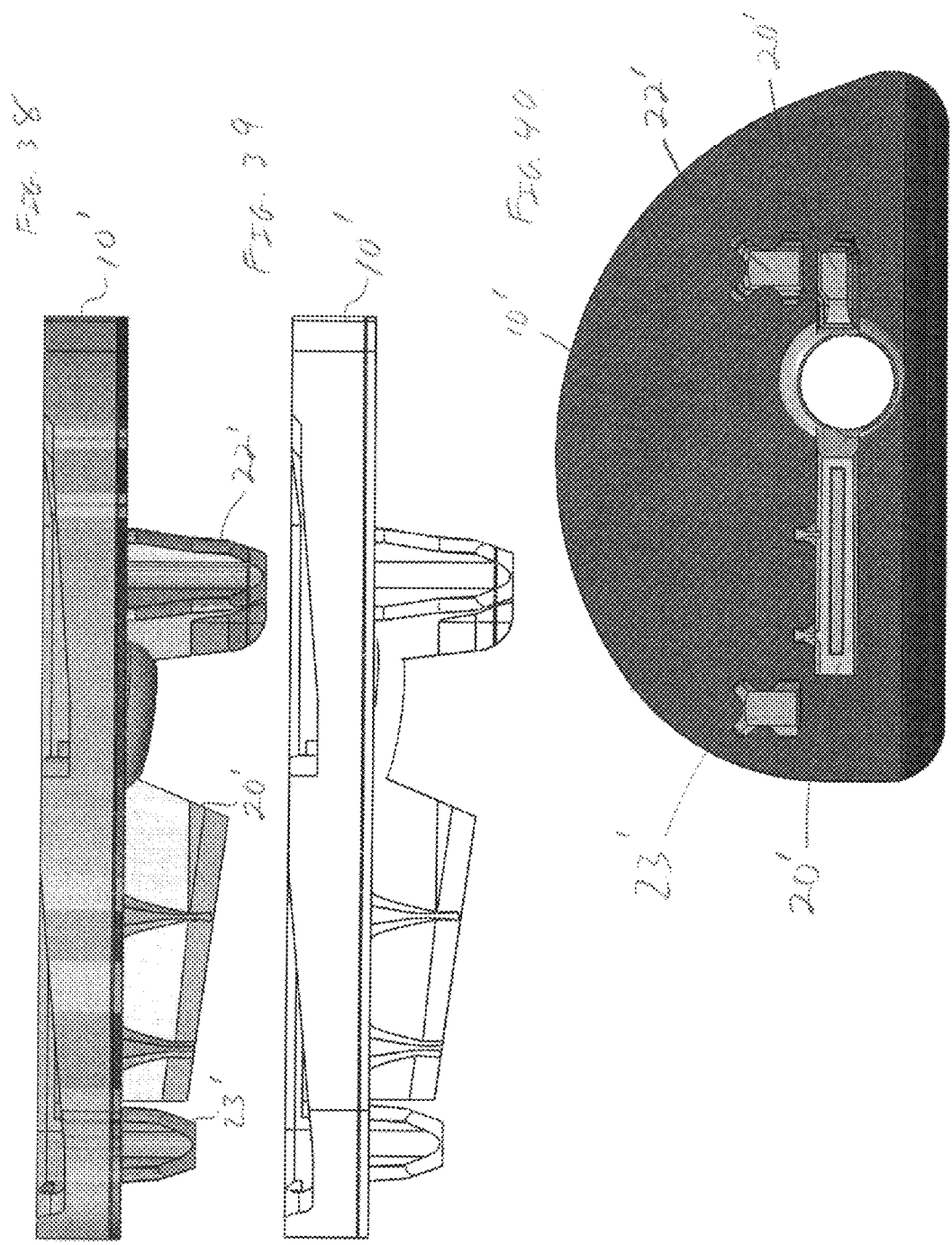

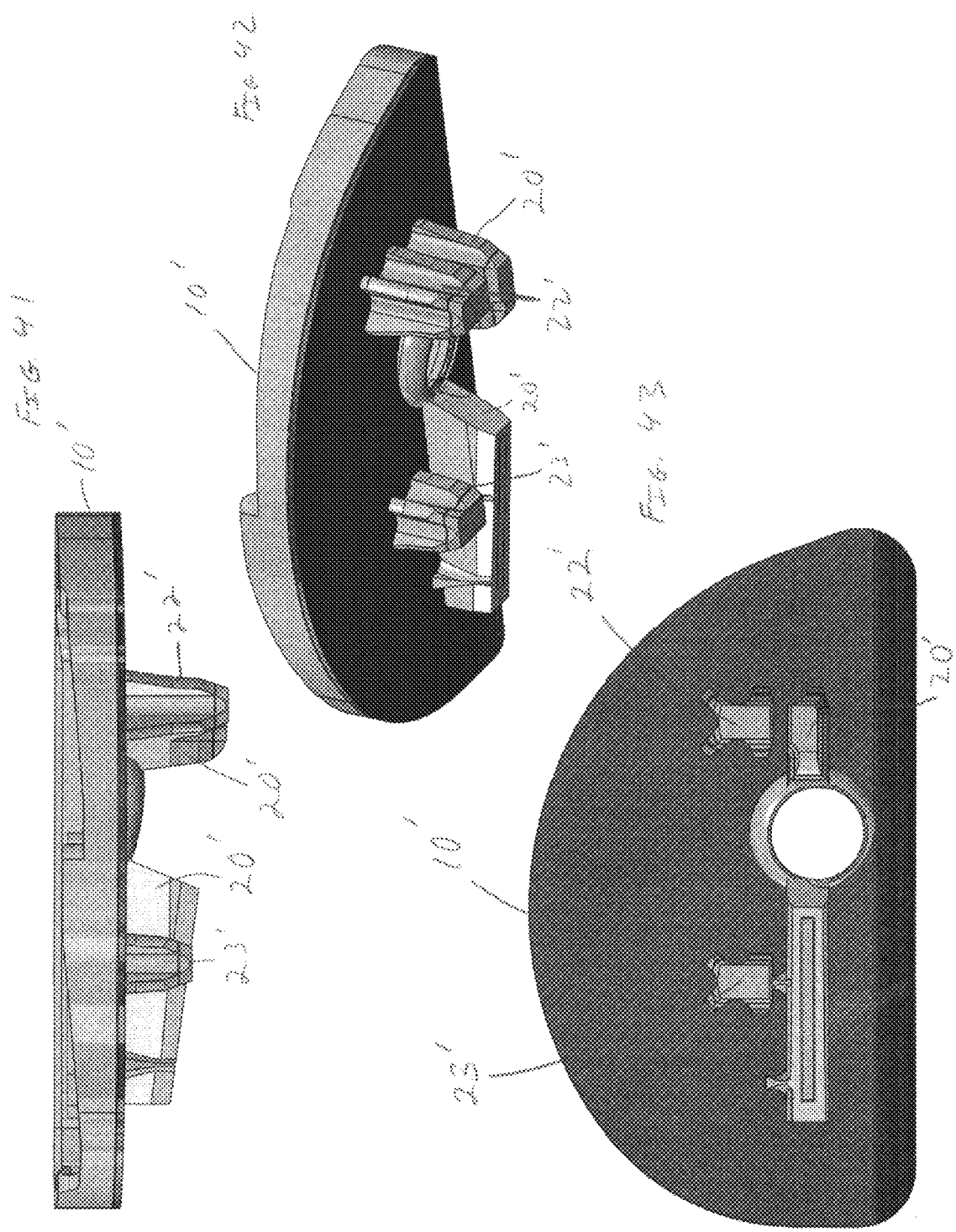

UNICONDYLAR TIBIAL KNEE IMPLANT

CROSS-REFERENCE TO RELATED APPLICATIONS

The present application claims the benefit of the filing date of U.S. Provisional Patent Application No. 61/794,339 filed Mar. 15, 2013, the disclosure of which is hereby incorporated herein by reference.

BACKGROUND OF THE INVENTION

The present invention relates generally to an orthopedic medical device implant. In particular, the present invention is related to a unicondylar knee implant system's tibial component.

Orthopedic knee implant systems have been used for many years to treat patients with knee joints that have been damaged by trauma or disease, such as osteoarthritis, rheumatoid arthritis, and avascular neurosis. A knee arthroplasty resects, cuts, or resurfaces the damaged sections of the knee and replaces them with an endoprosthetic or implant.

Most knee implant systems are tricompartmental implants and the surgical procedure used with tricompartmental implants is commonly known as total knee arthroplasty. These implants are known as tricompartmental implants because they are used when the knee joint is prepared to receive an implant by resurfacing or resecting the three articulating compartments, i.e., the medial and lateral femorotibial and the patellofemoral surfaces. Regardless of the type of implant used, all arthroplasties require the bone to be specifically prepared to receive a corresponding implant by resecting, resurfacing, or deforming the bone to accept the implant.

Unicondylar or unicompartmental knee implants have become of great interest in the orthopedic industry due to their less invasive nature and the maintaining of the other healthy knee compartments. Unicondylar knees resurface or resect typically the medial or lateral femorotibial articulating surfaces thus allowing preservation of the other compartments which may not be suffering from damage due to trauma or disease.

Generally, the clinical outcomes for unicondylar knee implants have varied. Studies have reported long term survival rates for unicondylar implants to be less than that of comparable total knee implants. One particular cause for such discrepancies is due to the bone cement fixation technique associated with the tibial implant. Another cause is the limitations on longer term cement fixation integrity. And, another cause is the non-physiological tibial bone loading patterns of a required metal backed tibial component that is relatively stiff compared to the surrounding bone.

The development of orthopedic implant designs has been moving towards meeting the requirements of high demand patients. Patients today are requiring more from their implants and since patients are living longer, they are requiring implants to last longer. Accordingly, developments have been made in materials used to make orthopedic implants to improve implant survival rates, such as highly porous metals for biological bone fixation.

Orthopedic devices are mated with host bone by either cementing them in place using methyl methacrylate, generally termed bone cement, or by providing a rough or porous surface on the device for bone tissue to grow into, generally termed press-fit or cementless.

The use of bone cement in attaching a prosthesis within or onto a prepared bone provides an excellent immediate fixation but has various disadvantages that appear over time. Physical loads are repeatedly applied to the implant over its life. If bone cement is used to secure a unicompartmental knee prosthesis, the bone cement may fatigue and fracture under the repeated loading. In some instances, degradation of the bone cement integrity may cause the device to become loose, thereby necessitating replacement. Old bone cement must be removed from the host bone as part of the implant replacement procedure. This procedure can be complex, time consuming and potentially destructive to healthy bone structures surrounding the implant. Furthermore, conventional bone cement is cured after it has been dispensed into the patient's joint. Loose undetected cement fragments can remain in the joint space and, with patient mobility over time, increase the degradation rate of articulating implant surfaces.

Recognizing the disadvantages of cement fixation techniques, prior art devices have been developed that utilize mechanical attachment means to join an implant to bone for immediate stabilization. Various implant surface treatments intended to bond with bone biologically for long term stable attachment have proven successful. A simple technique of mechanically securing an implant, is to affix it within the bone with screws or other mechanical fasteners. However, due to the nature of the bone surrounding the surgical site, and other limiting factors such as artery location and the like, screws can only be applied in certain limited regions. The use of a screw for implant fixation should be considered only as an option by the surgeon depending upon implant placement and bone quality.

Primary fixation of an implant should come from a high friction interface with the prepared bone and in the long term with bone tissue ingrowth into a porous portion of the device. Specific instruments and surgical procedures are developed to match the implant and bone preparation. Often the bone cuts are undersized so that the implant or a portion of the implant such as a peg or keel is "press fit" into the bone. This assures an intimate contact between bone and implant. A high friction coating or porous portion of the implant assists with immediate bone fixation by mechanically locking the device in place. High friction will also resist any loading which may displace the device prior to bone ingrowth and more permanent biological fixation.

Prior art has established many methods for producing a high friction porous layer for implant designs. The use of metal beads, particles or wires which are metalurgically bonded to the implant surface is common. Plasma coating of metal surfaces with rough layers of metal particles is also utilized. More recently, porous metals of various chemical make up and structure have been developed which mimic the design of bone trabecular structure. These materials have been shown to have superior bone ingrowth results and should lead to improved implant fixation.

BRIEF SUMMARY OF THE INVENTION

In accordance with a preferred embodiment, the present invention provides for a unicondylar tibial implant. The tibial implant includes a tibial keel positioned on a surface of the tibial implant to be submerged into prepared bone with a first projection extending along its lengthwise direction and a second projection extending along a direction perpendicular to the first projection. The first projection may be interrupted by a void to allow clearance for another implant or instrument. The second projection intersects the first projection. The tibial implant can be fabricated from a metal, a polymer, a biodegradable material, a porous metal material, or combinations thereof. The device as described could be produced through additive manufacturing techniques such as direct metal laser sintering. The foregoing description of the present invention is provided for the tibial implant when used on the medial condyle. However, the preferred embodiment can also be used on the lateral condyle, and when utilized in such a manner would have some features reversed in orientation. A description of the medial component features of the tibial implant is provided only for simplification.

The tibial keel is configured as an anterior-posterior projection with an intersecting keel segment that extends about a medial-lateral direction. The tibial keel is comprised of a solid material on a bone interfacing leading edge of the tibial keel i.e., a solid end portion, with the tibial keel having a porous material between the tibial tray and the solid end portion of the tibial keel. The tibial implant can optionally include a bone screw to secure the tibial implant to bone.

In accordance with another preferred embodiment, the present invention provides for a unicondylar tibial implant having a tibial keel configured as an anterior-posterior projection with at its most anterior aspect being an intersecting keel in the medial-lateral direction. The tibial keel is comprised of a solid material on a leading edge of the keel and porous material between the tibial tray and the solid end portion of the keel, and smaller protrusions on the medial facing portion of the tibial keel at the intersection of the tibial keel and tibial tray. The tibial implant is fabricated from a metal, a polymer and/or a biodegradable material. The tibial implant can optionally include a bone screw to secure the tibial implant to bone.

In accordance with yet another preferred embodiment, the present invention provides for a unicondylar tibial implant having a tibial keel configured as an anterior-posterior projection with at its most anterior aspect being an intersecting keel in the medial-lateral direction. The tibial keel is comprised of a solid material on the leading edge of the keel and porous material between the tibial tray and a solid end portion of the keel being implanted into an interference-fit created by an undersized preparation in the bone. The tibial implant is fabricated from a metal, a polymer and/or a biodegradable material. The tibial implant can optionally include a bone screw to secure the tibial implant to bone.

In accordance with another preferred embodiment, the present invention provides for a unicondylar tibial implant having a tibial keel configured as an anterior-posterior projection with at its most anterior aspect being an intersecting keel in the medial-lateral direction. The tibial keel is comprised of a solid material on a leading edge of the keel and porous material between the tibial tray and a solid end portion of the keel, and smaller protrusions on the medial facing portion of the keel at the intersection of the tibial keel and tibial tray where the protrusions preferentially force the tibial implant into the bone prepared about a resected mid-tibial eminence. The tibial implant is implanted into an interference fit created by an undersized preparation in the bone. The tibial implant is fabricated from a metal, a polymer and/or a biodegradable material. The tibial implant can optionally include a bone screw to secure the tibial implant to bone.

In accordance with yet another preferred embodiment, the present invention provides for a keel for a unicondylar tibial implant. The keel is connected to the tibial tray of the tibial implant and includes smaller protrusions on a medial facing portion of the keel at an intersection of the keel and the tibial tray where the protrusions push the tibial implant into the bone prepared about a resected tibial eminence. The keel is fabricated from a metal, a polymer and/or a biodegradable material. The tibial implant can optionally include a bone screw to secure the tibial implant to bone.

In accordance with another preferred embodiment, the present invention provides for a unicondylar tibial implant having a tibial tray with a porous keel and protrusions extending from the keel. The tibial tray accepts a polyethylene tibial bearing having an articulating surface for articulating with a femoral component. The tibial bearing can be a modular polyethylene tibial bearing. The tibial implant and tibial bearing can also be formed as a monoblock component. Alternatively, the tibial tray with a porous keel can be formed out of a singular biomaterial which is also used to form the tibial bearing. The tibial implant can optionally include a bone screw to secure the tibial implant to bone.

In accordance with yet another preferred embodiment, the present invention provides for a unicondylar tibial implant having at least one section of material that in its normal state forms at least one uninterrupted surface of the implant that is separable from the greater bulk of the tibial implant in a predictable shape defined by the presence of a shear section. The shear section of material when removed exposes a passageway for at least one additional implant, such as a bone screw. The removal of the shear section also exposes a passageway for surgical instrumentation, for the application of osteobiologic materials or for the application of bone cement.

In accordance with another preferred embodiment, the present invention provides for the ornamental design of a unicondylar tibial implant as shown and described in the figures below.

BRIEF DESCRIPTION OF THE SEVERAL VIEWS OF THE DRAWINGS

The foregoing summary, as well as the following detailed description of the preferred embodiments of the invention, will be better understood when read in conjunction with the appended drawings. For the purpose of illustrating the invention, there are shown in the drawings embodiments which are presently preferred. It should be understood, however, that the invention is not limited to the precise arrangements and instrumentalities shown.

DETAILED DESCRIPTION OF THE DRAWINGS

Figure 19:
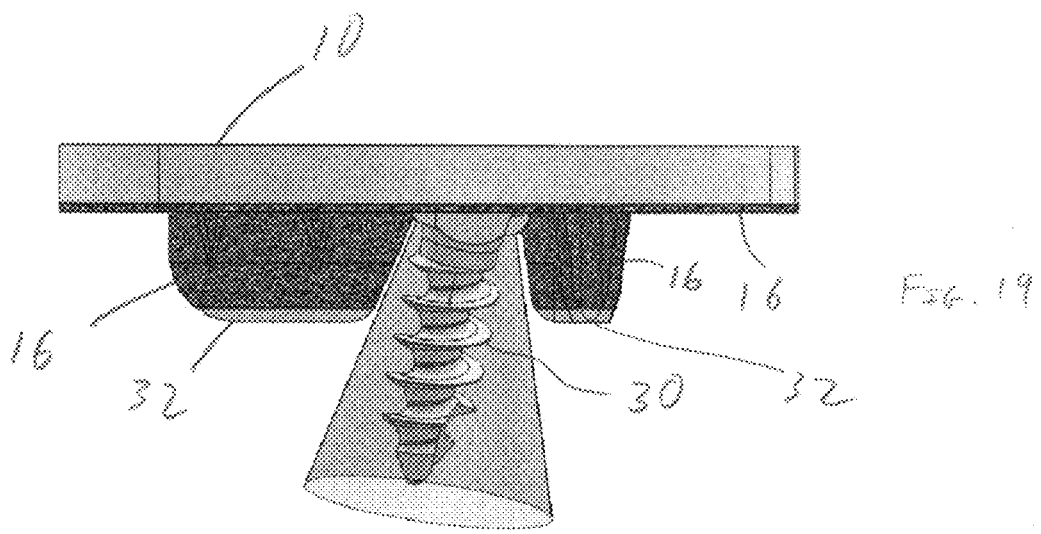
Figure 20:
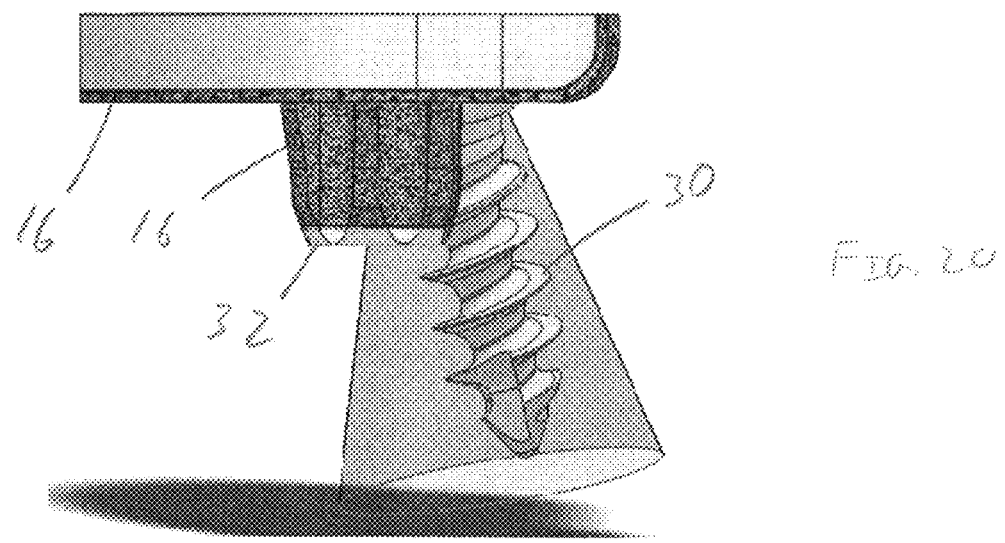
Figure 21:
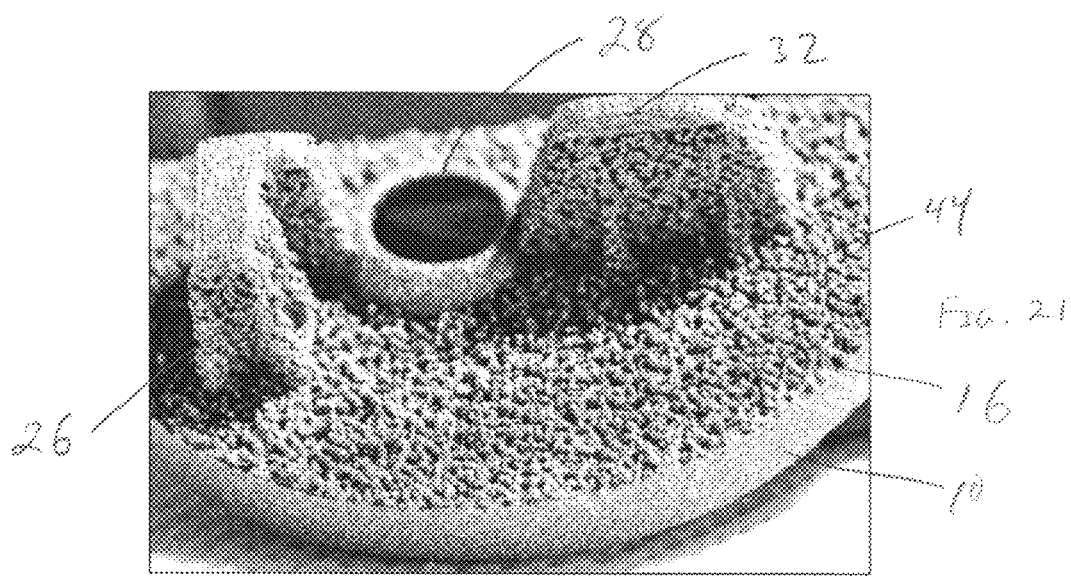
Figure 22:
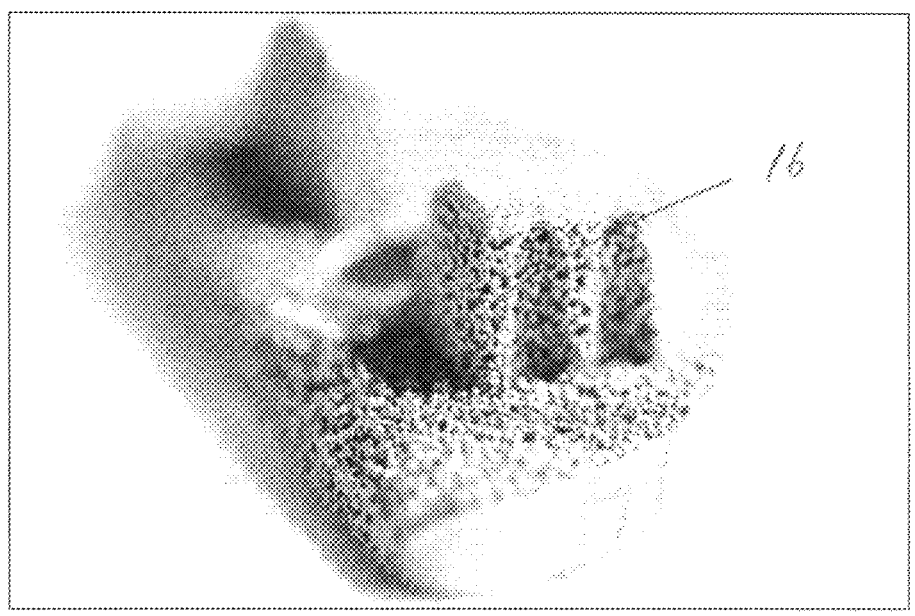
Figure 23:
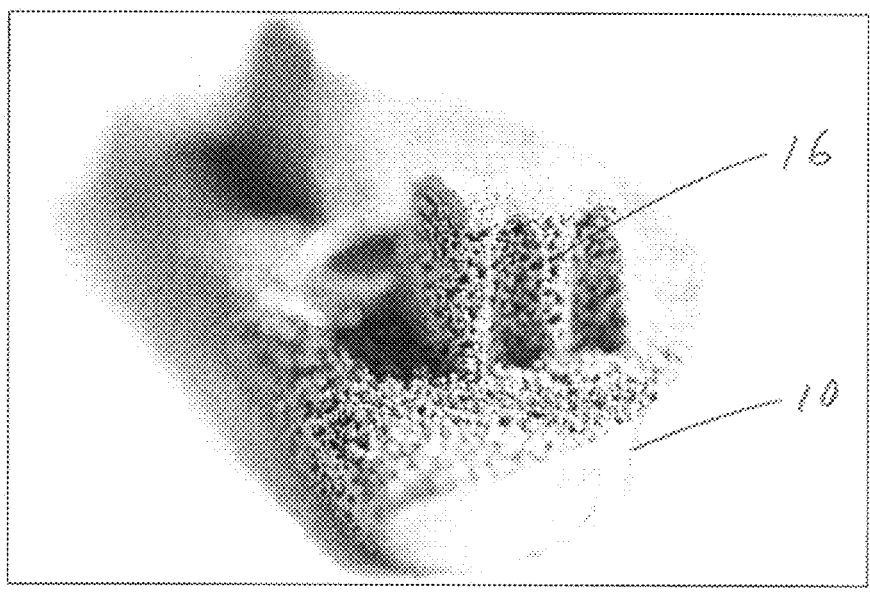
Figure 24:
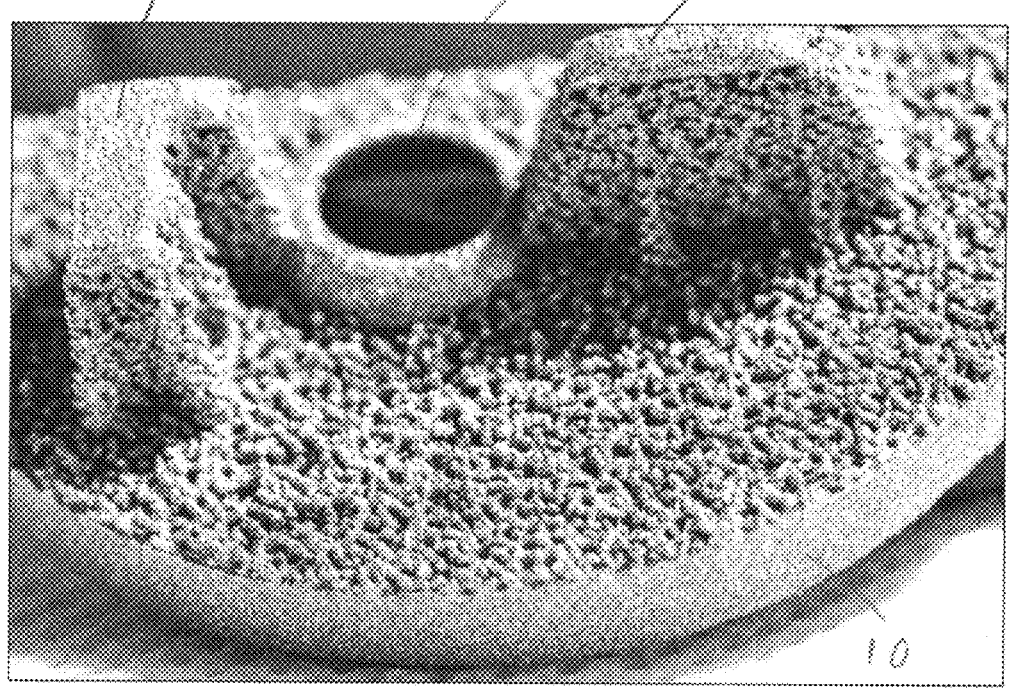
Figure 27:
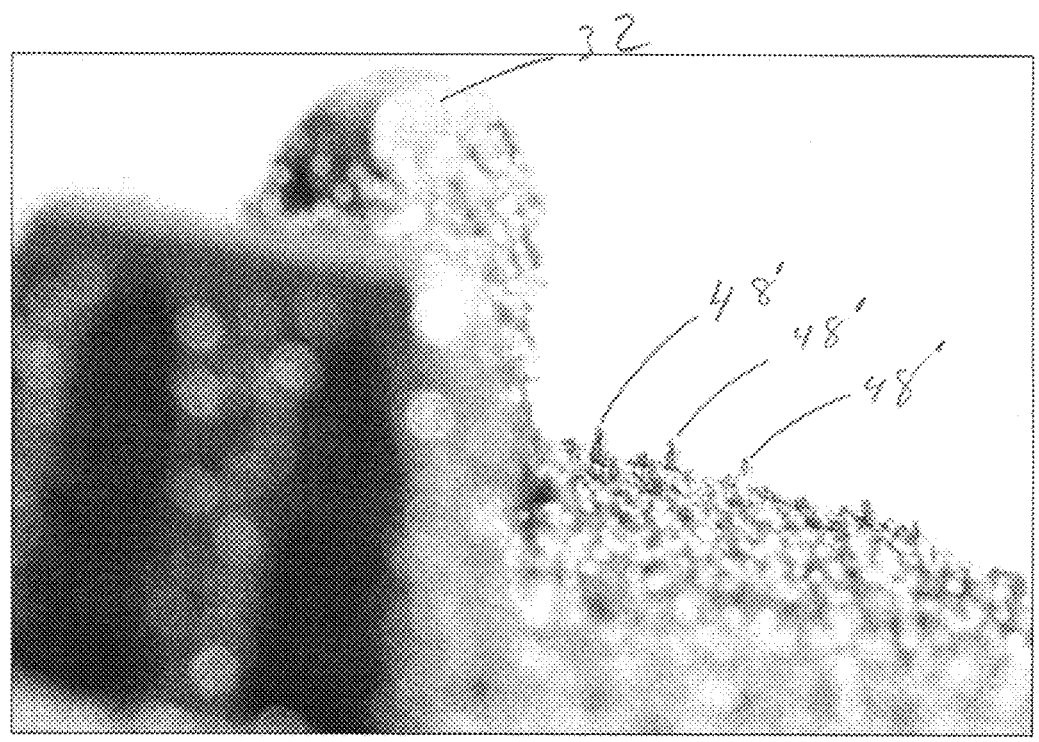
Figure 28:
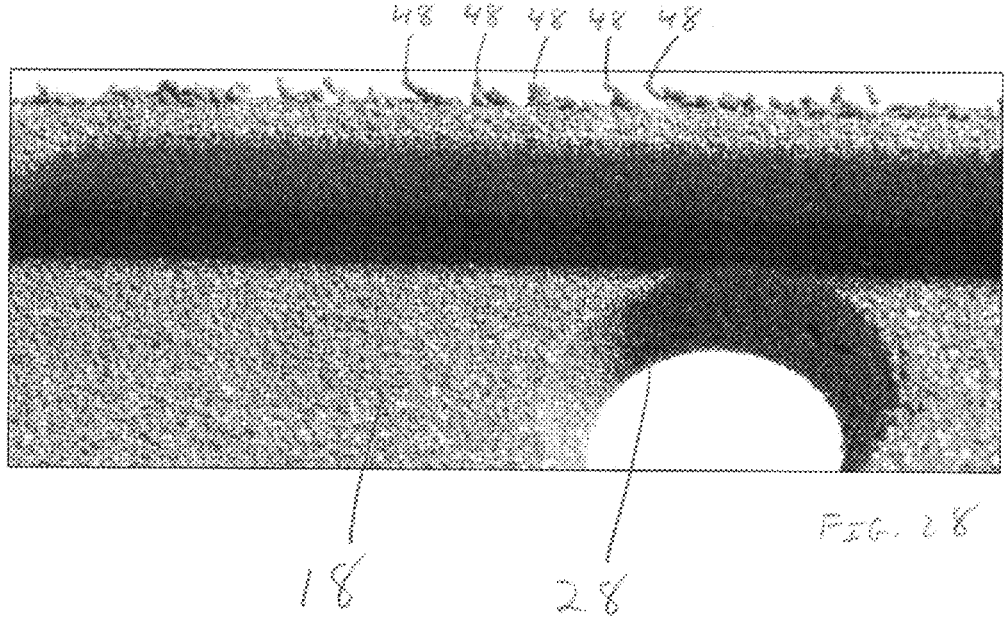
Figure 29:
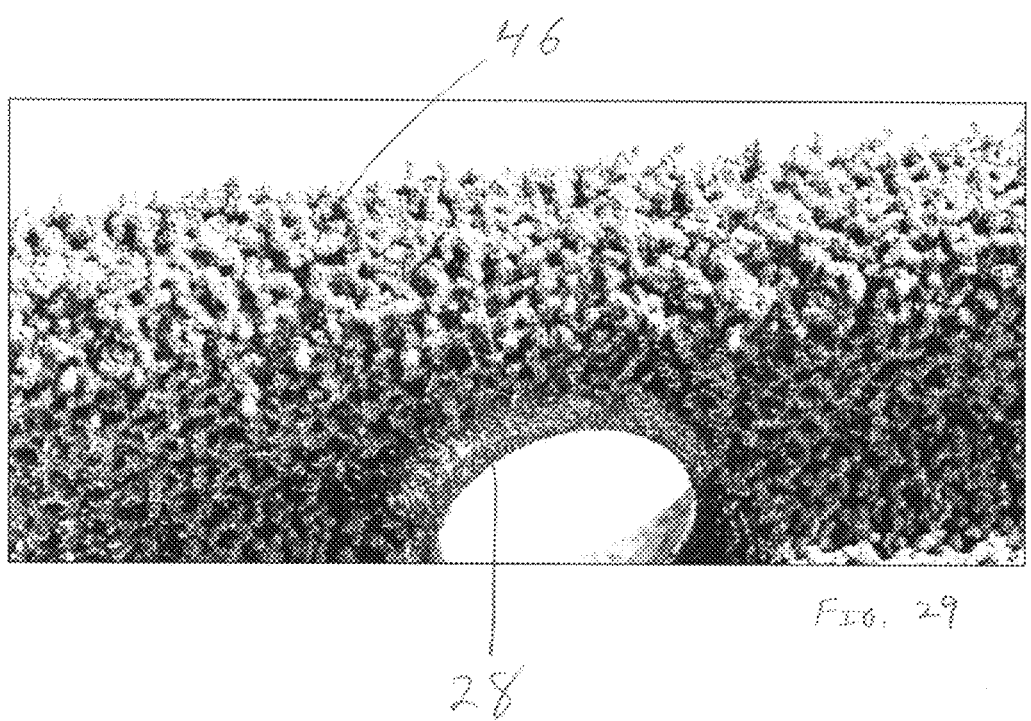
Figure 30:
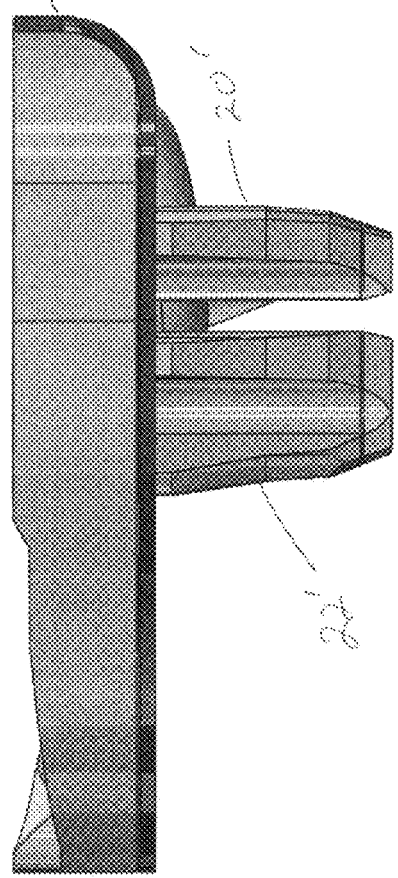
Figure 31:
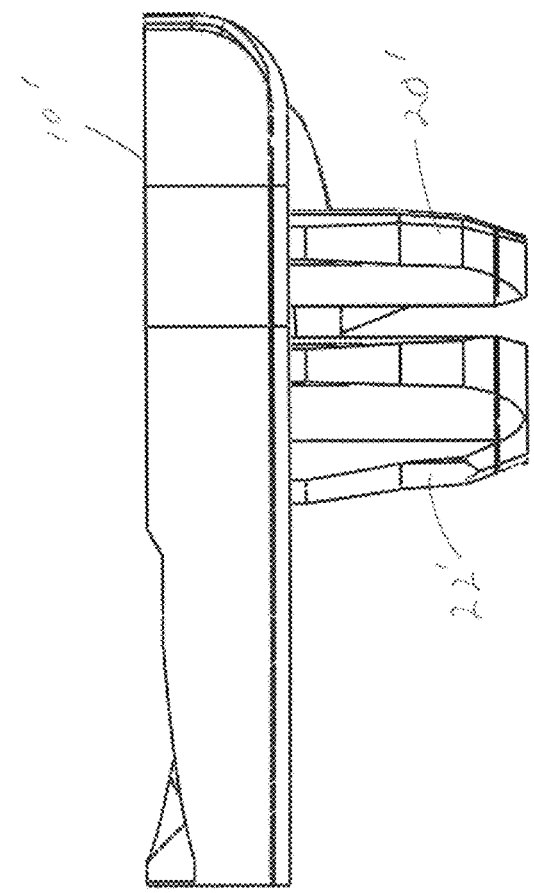

FIGS. 1-8 illustrate a unicondylar tibial implant assembly in accordance with a preferred embodiment of the present invention;

FIGS. 9-18 illustrate a unicondylar tibial implant of the tibial implant assembly of FIGS. 1-8;

FIGS. 19 and 20 illustrate the unicondylar tibial implant of FIGS. 9-18 with a bone screw positioned within a through hole of the tibial implant;

FIGS. 21-29 are highly magnified photographic images of a porous portion of the unicondylar tibial implant of FIGS. 9-18;

FIGS. 30-37 illustrate a unicondylar tibial implant in accordance with another aspect of the preferred embodiment of the present invention;

FIGS. 38-40 illustrate a unicondylar tibial implant in accordance with yet another aspect of the preferred embodiment of the present invention; and FIGS. 41-43 illustrate a unicondylar tibial implant in accordance with another a further aspect of the preferred embodiment of the present invention.

DETAILED DESCRIPTION OF THE INVENTION

Reference will now be made in detail to the preferred embodiments of the present invention illustrated in the accompanying drawings. Wherever possible, the same or like reference numbers will be used throughout the drawings to refer to the same or like features. It should be noted that the drawings are in simplified form and are not drawn to precise scale. In reference to the disclosure herein, for purposes of convenience and clarity only, directional terms such as top, bottom, above, below and diagonal, are used with respect to the accompanying drawings. Such directional terms used in conjunction with the following description of the drawings should not be construed to limit the scope of the invention in any manner not explicitly set forth. Additionally, the term "a," as used in the specification, means "at least one." The terminology includes the words above specifically mentioned, derivatives thereof, and words of similar import.

Partial knee implants, also known as unicondylar or unicompartmental knee implants, replace either a medial or lateral compartment of a knee joint by resurfacing, either by itself or in conjunction with a resurfacing of the femoral condyle and an articulating surface of a proximal tibia with an engineered implant. The preparation of the bone to accept such implants may be facilitated by instrumentation such as bone files, burrs, saws, punches, and/or computer assisted instrumentation/navigation systems. Once the bone is prepared, the implant may be secured to the bone by bone cement which bonds to the implant and impregnates the bone resulting in fixation of the implant to the bone interface.

In order to remove bone cement from the surgical procedure of implanting partial knee implants, implants have been designed for fixation directly to the bone. Such fixation without bone cement is known as cementless fixation or press-fit fixation. The challenge of cementless fixation of tibial implant components is to have acceptable initial stability upon implantation to allow patient mobility immediately or a short time after surgery and promote adequate biologic fixation of the implant to the bone long term. The initial stability and long term fixation are requirements of the implant to reduce the incidence of implant loosening and reduce patient post-operative pain over time.

The present invention illustrated in FIGS. 1-43 discloses preferred embodiments of a unicondylar tibial implant assembly 5 having a unicondylar tibial implant 10 and a unicondylar tibial implant bearing 12. The unicondylar tibial implant 10 has been developed primarily for cementless application and includes a unique bone interfacing tibial keel 14 and a porous structured biomaterial interface i.e., a porous portion 16 (FIGS. 21-29). The tibial implant 10 can be constructed from any combination of solid metal, porous metal, polymers or resorbable materials.

For purposes of convenience only, and not by way of limitation, the foregoing description of the preferred embodiments of the unicondylar tibial implant assembly 5 will be described and illustrated with respect to a unicondylar tibial implant assembly 5 for a medial tibial condyle. However, the foregoing description and features of the unicondylar tibial implant assembly 5 are equally applicable to a unicondylar tibial implant assembly for a lateral condyle, such similar features of the lateral unicondylar tibial implant assembly being substantially mirror images of such features of the medial unicondylar tibial implant assembly.

The tibial keel 14 is located on an undersurface of a tibial tray 18 of the tibial implant 10 which contacts a resected tibia bone (not shown). The tibial keel 14 is generally submerged into the bone to which the tibial implant 10 is to be implanted thereon. The tibial keel 14 can prepare its own cavity in the bone as it is inserted into the resected tibia or it can occupy cavities within the bone previously prepared by instrumentation or other implants. Any pre-cavities for receiving the tibial keel 14 when pre-prepared are generally smaller in size than the tibial keel 14 so as to generate compressive forces between the bone interface and the tibial keel 14 and increase frictional forces between the bone and the tibial keel 14. That is, the tibial keel 14 is press-fitted into the bone.

Preferably, the tibial keel 14 is located on an underside of the tibial tray 18 of the tibial implant 10 and constructed out of a combination of a solid metal substrate and a porous portion 16 on the surfaces of the tibial keel 14.

The tibial keel 14 is best shown in FIGS. 2, 4-10 and 14-20 and includes a first projection 20 which is generally planar and has a height which corresponds to a depth within a prepared bone to which the tibial keel 14 will protrude into. The tibial keel 14 also includes a second projection 22 which is generally planar, has a height which corresponds to a depth within a prepared bone to which the tibial keel 14 will protrude into and is substantially perpendicular to the first projection 20. The heights of first and second projections 20, 22 of the tibial keel 14 may be variable to accommodate access limitations while maximizing the fixation of the tibial implant 10 into bone. Preferably, the tibial keel 14 is positioned on an underside or inferior surface 24 of the tibial tray 18 with the first projection 20 running along the anterior-posterior direction. The second projection 22 intersects the first projection 20 towards the anterior edge of the first projection 20. Both of the first and second projections 20, 22 of the tibial keel are substantially normal to the underside of the tibial tray 18. Further, the first protrusion 20 can be configured to have a height that varies along its length.

Figure 1:
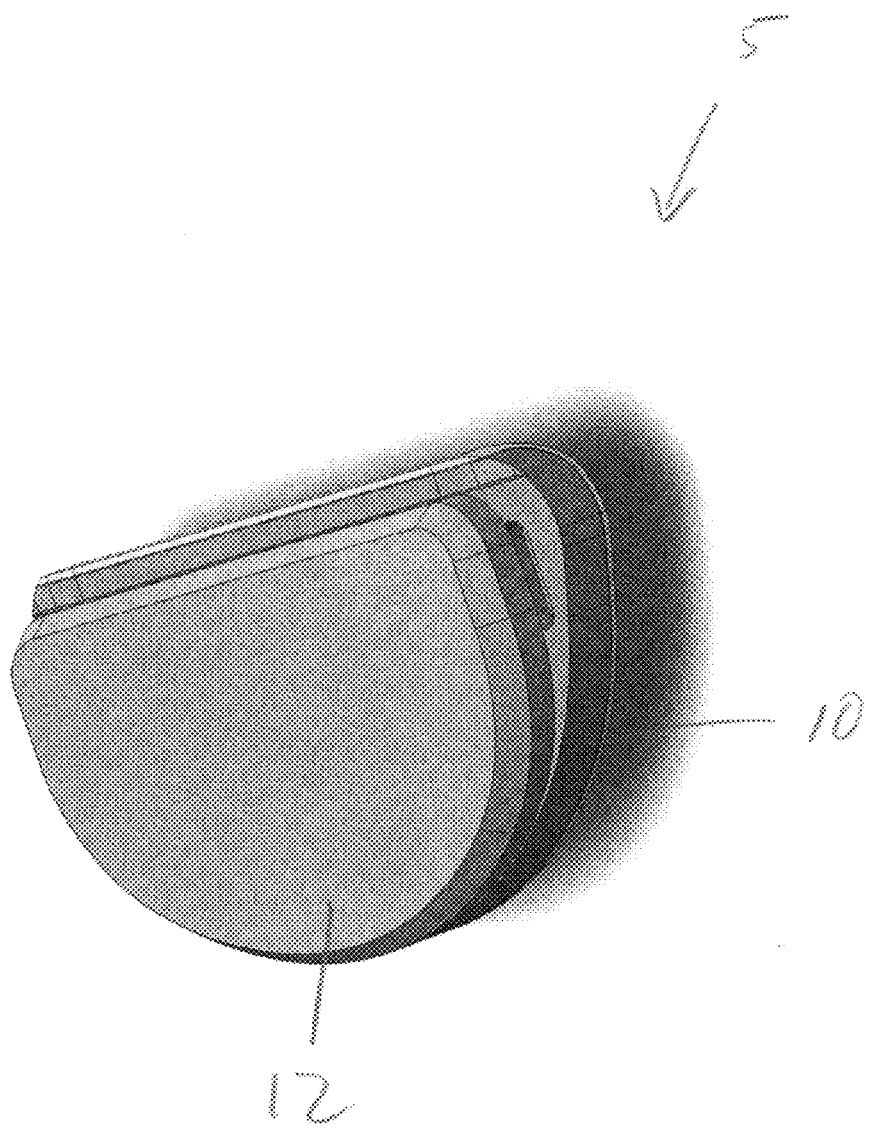
Figure 2:
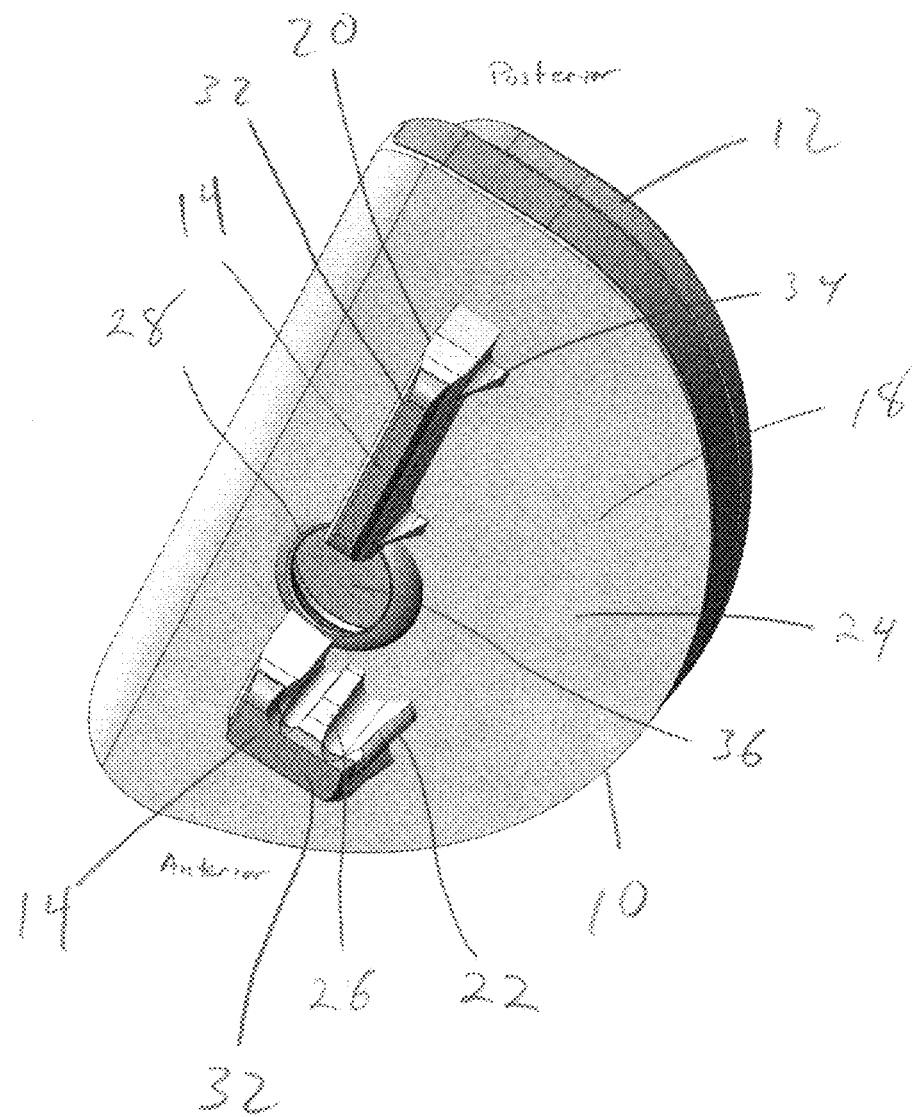
Figure 3:
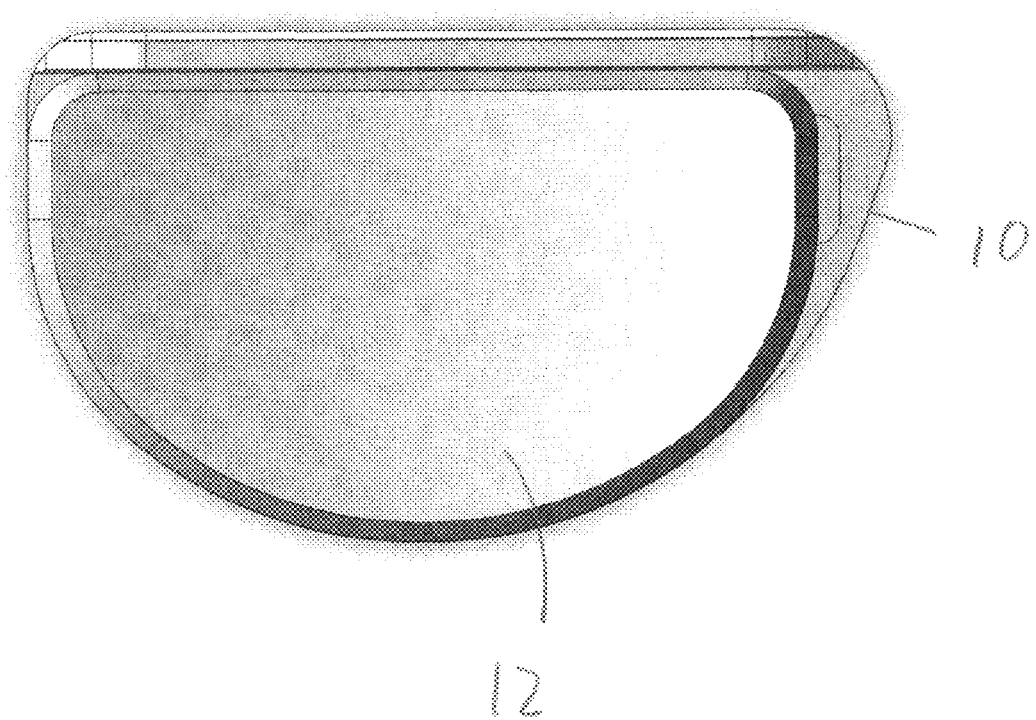
Figure 4:
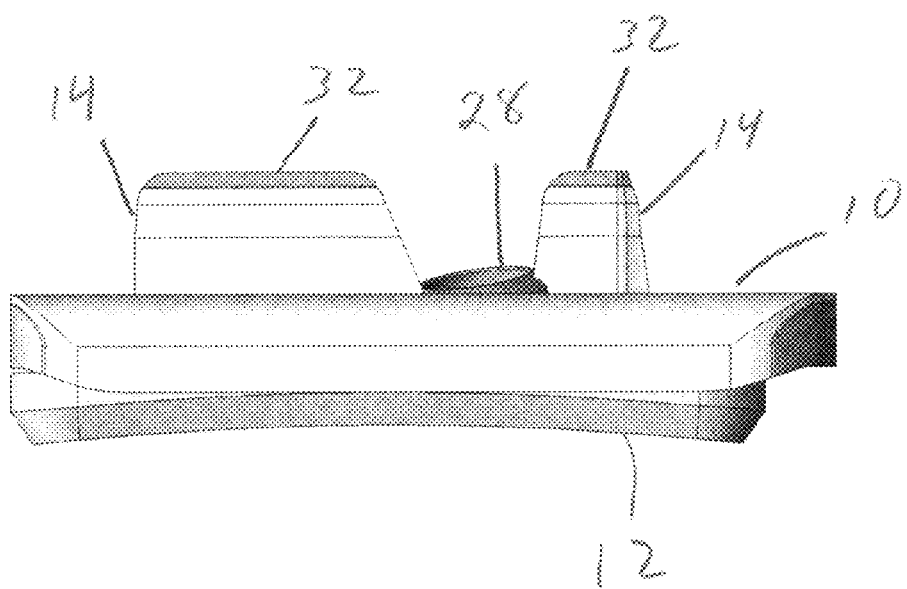
Figure 5:
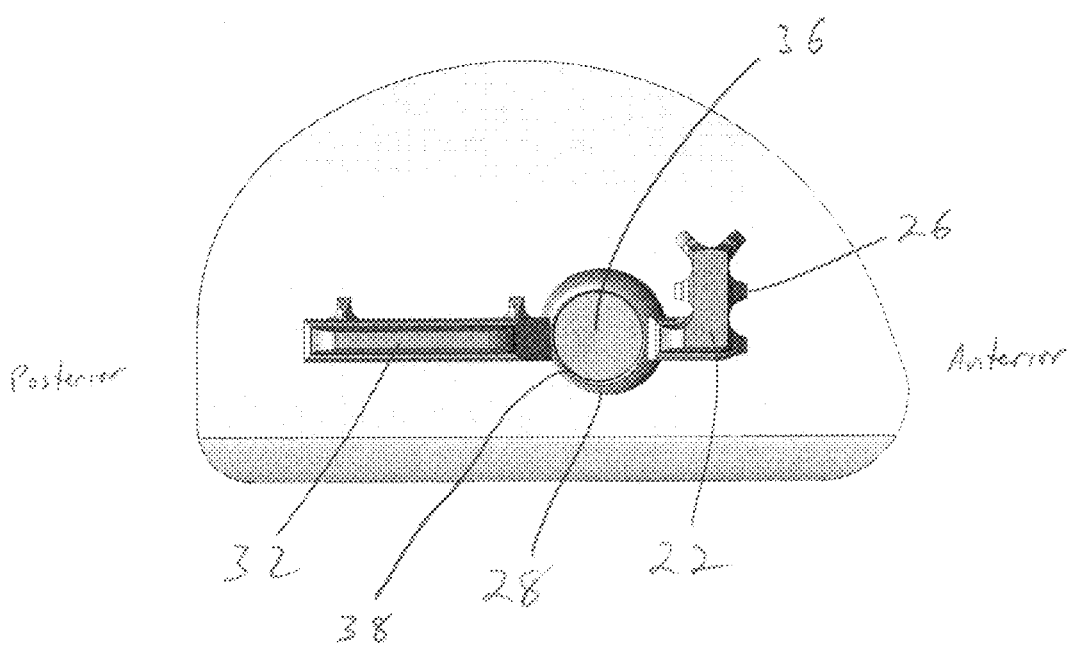
Figure 6:
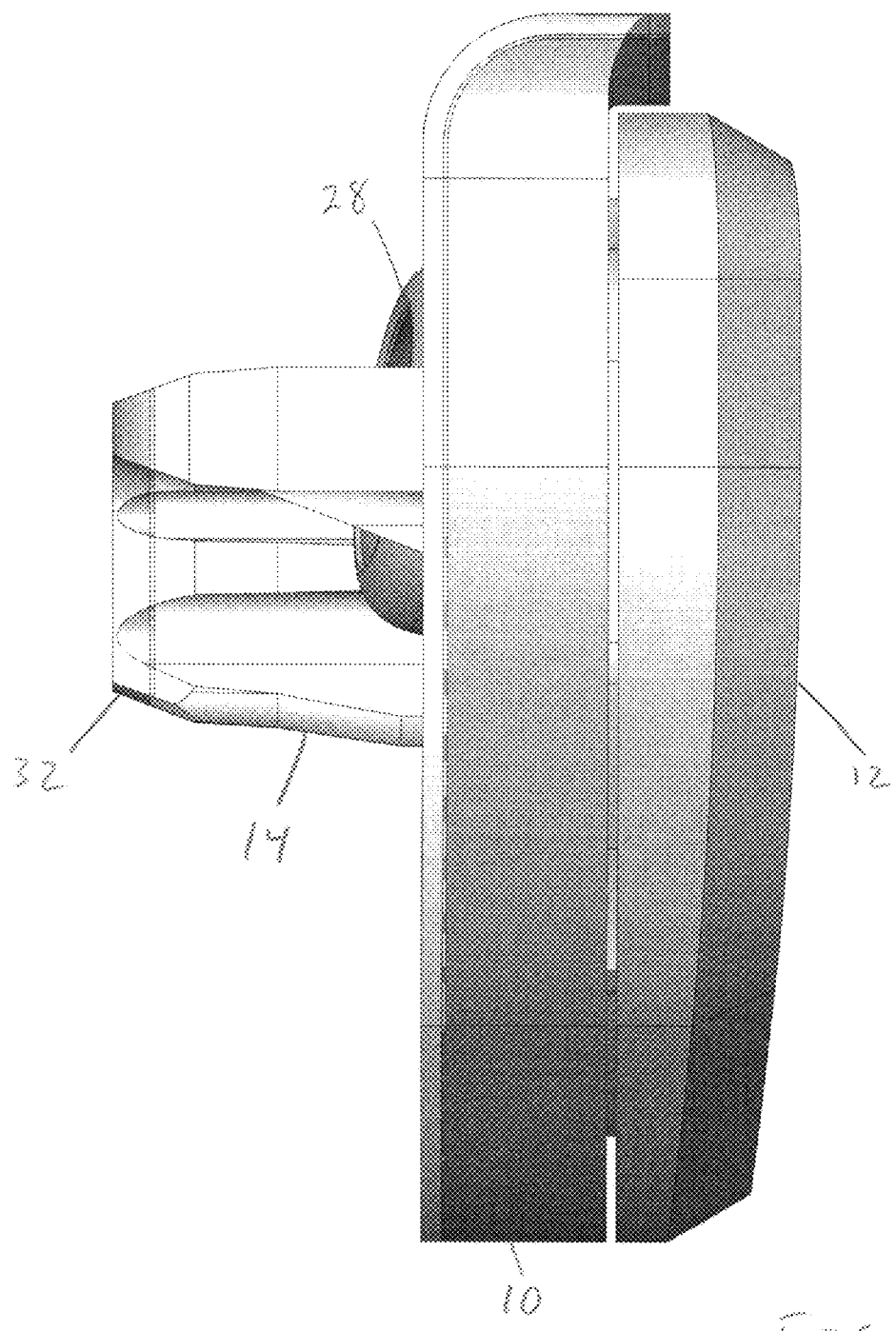

Each of the first and second protrusions 20, 22 of the tibial implant 10 can be configured to have one or more extensions i.e., a plurality of extensions 26. FIGS. 2 and 5 illustrate the extensions 26 extending from the second protrusion 22. The extensions 26 that emanate from the protrusions are oriented out of plane with the protrusion. That is, the extensions 26 extend outwardly from the lateral surfaces of the protrusions. The extensions 26 are designed to create and fill cavities within the bone so as to create and maximize compressive frictional forces between the tibial keel 14 and the surrounding bone. The extensions 26 are preferably located so that resultant forces during insertion of the tibial implant 10 into a resected tibia bias the position of the tibial implant 10 in a predetermined or desired direction. The extensions 26 are configured as substantially wedge shaped extensions that extend along substantially the entire height of the keel. Further, the extensions 26 preferably tapered in the distal direction. The plurality of extensions 26 on the second protrusion 22 are spaced apart from each other and substantially circumscribes the second protrusion 22. Preferably, the second protrusion includes five extensions 26, but can include more or less than five.

The extensions 26 are preferably located around the periphery of both the first and second protrusions 20, 22 with a higher number of extensions 26 or higher density of extensions emanating from the second protrusion 22 located about the anterior region of the tibial implant 10 where higher frictional forces are able to make a greater contribution to address anterior lift-off stability issues of the tibial implant 10 when implanted within the bone. The number of extensions 26 is greater on the sides of the protrusion 22 that face away from a central region of the tibial implant 10 so that bone reaction forces will push/direct the tibial implant 10 into the central region of the tibia.

The tibial implant 10 can optionally be configured with a through hole 28 (FIGS. 2, 5 and 21) through which another device, instrument or material e.g., a bone screw 30 (FIGS. 19 and 20) can be inserted therethrough. The through hole 28 may pass through one or more of the protrusions 20, 22 thereby interrupting their general shape. However, material is removed from protrusions 20, 22 around or adjacent the through hole 28 to provide for clearance of the device, instrument or material to be inserted therethrough.

A solid edge 32 (FIGS. 2, 7 and 21) at the distal end of the tibial keel 14 prevents bone from growing into the tibial keel 14 from the bottom up. The majority of the surface area of the tibial implant 10 for fixing i.e., via bone ingrowth, the tibial implant 10 to the bone occurs at the perimeter of the tibial keel 14, i.e., the lateral side surfaces of the tibial keel 14. The bone which engages and contacts the bottom of the tibial keel 14 represents a small fraction of the overall surface area of the tibial implant 10.

That is, the tibial implant 10 is configured to prevent any bone ingrowth or fixation about a distal surface of the tibial keel 14 via the solid edge 32. Preventing bone ingrowth about the distal surface of the tibial keel 14 allows for easier removal of the implant, if necessary, since bone ingrowth on such distal surfaces of the tibial keel 14 represents areas that are most problematic to achieving separation of the implant from bone during revision procedures. In other words, as an implant is pulled out of bone, bony ingrowth into the bottom portion of the tibial keel might not separate from the greater volume of the bone exactly at the implant interface but rather somewhere deeper within the volume of bone beneath the implant. If this occurs during implant removal, the additional bone that would otherwise be inadvertently removed would complicate the revision procedure and drive the use of more significant revision components.

The general shape of the tibial keel 14 is designed to maximize surface area to volume ratio for the tibial keel 14 to enhance bone ingrowth thereto while minimizing the amount of bone removal during bone preparation. The amount of surface area available for bone ingrowth is important for both short and long term fixation of the implant to the bone. Short term fixation is achieved by "press-fitting" a larger body into a smaller preparation. Once in place, the residual stresses from the compressed bone around the tibial keel 14 increase the frictional forces against the tibial keel 14 and increase the stability of the tibial implant 10 into the prepared bone. Increasing the surface area over which the press-fit interference is effective helps to increase the total frictional forces available to contribute to stability of the implant and to distribute frictional forces over a greater effective area of the tibial implant 10.

Long term fixation of the tibial implant 10 is enhanced by the areas of the tibial implant 10 having the porous structure and surface, hereafter referred to as 'porous metal' 26. As the bone remodels and grows into the porous metal 26, the frictional retention forces will be replaced and/or supplemented with bone ingrowth. The degree of this fixation via bone ingrowth is, in part, a function of the amount and distribution of the porous metal surface area available for ingrowth. The large distributed tibial keel surface area thereby provides a structure for increased stability via a larger area of bone ingrowth.

Figure 7:
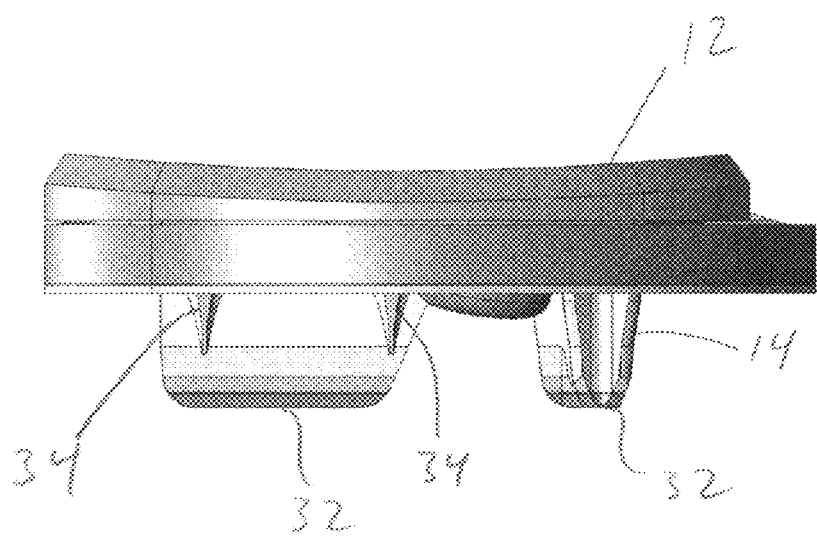
Figure 8:
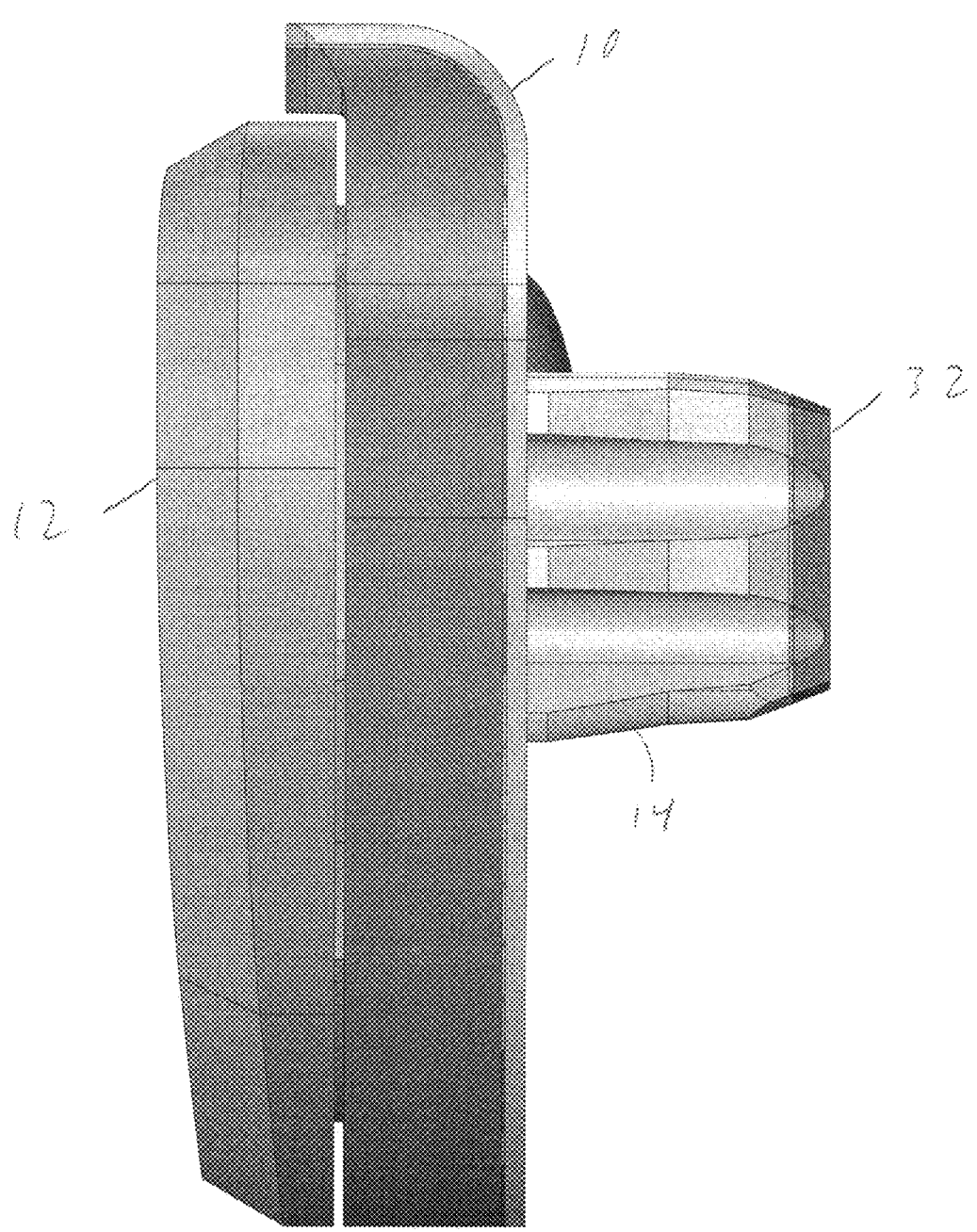
Figure 9:
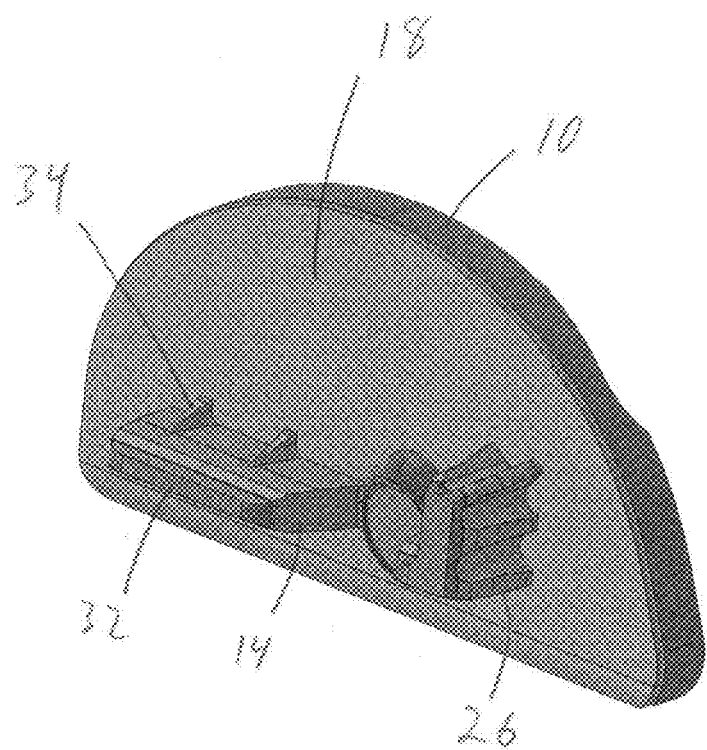
Figure 10:
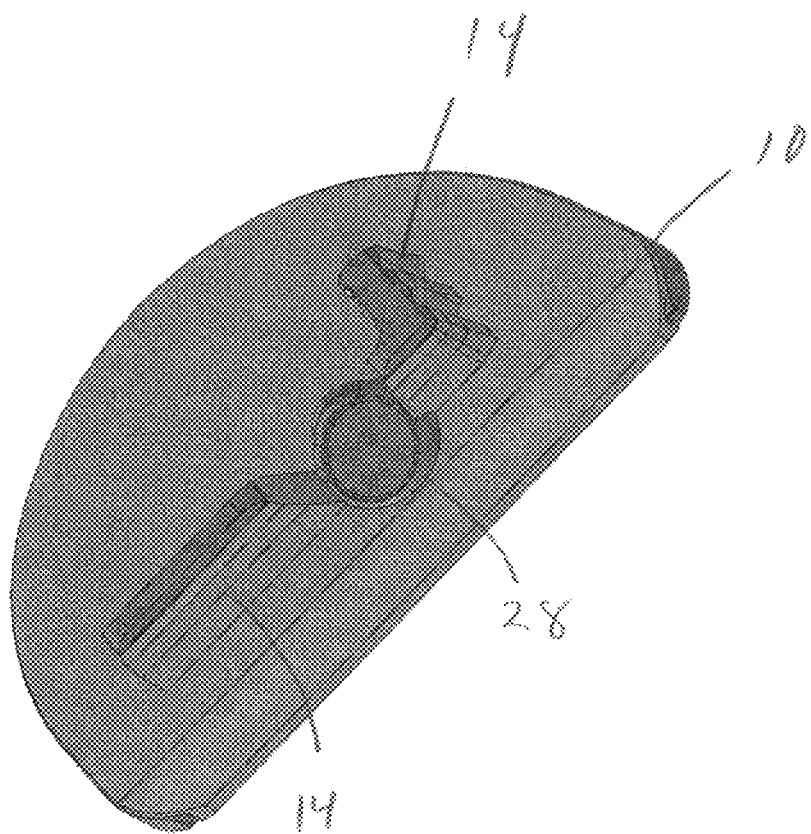
Figure 11:
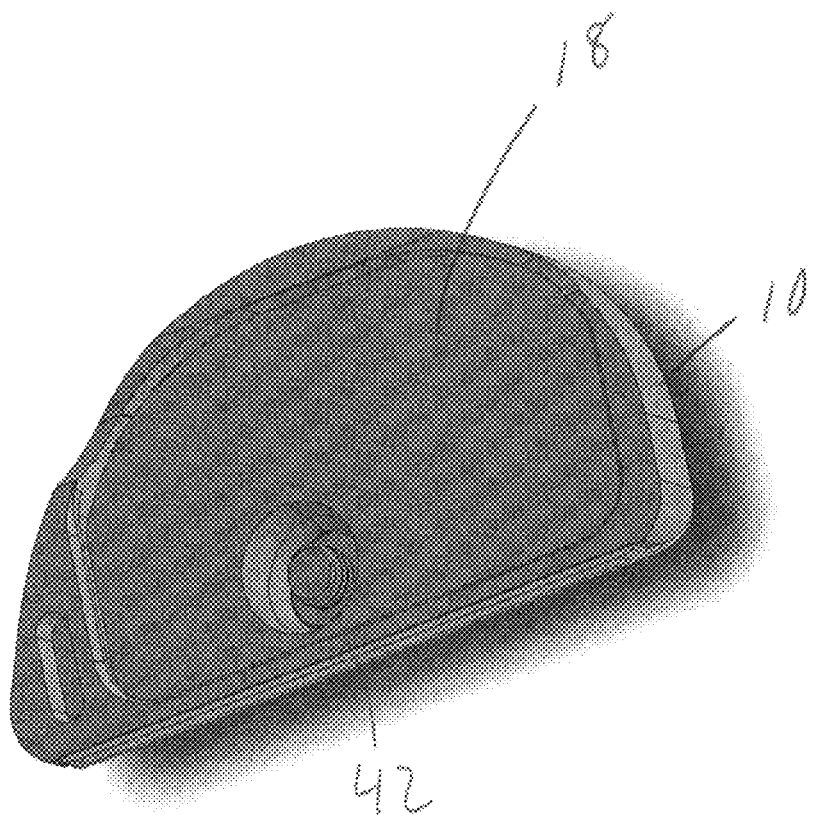
Figure 12:
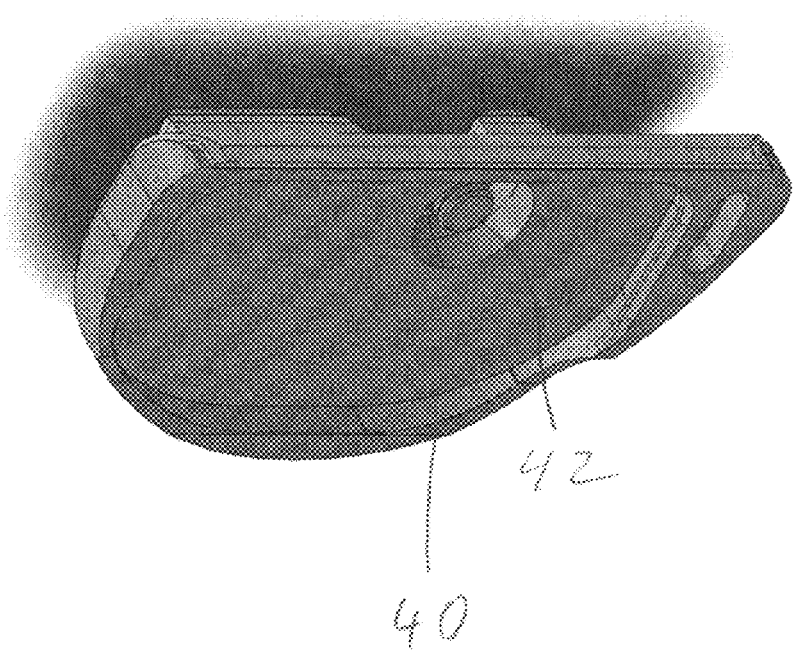
Figure 13:
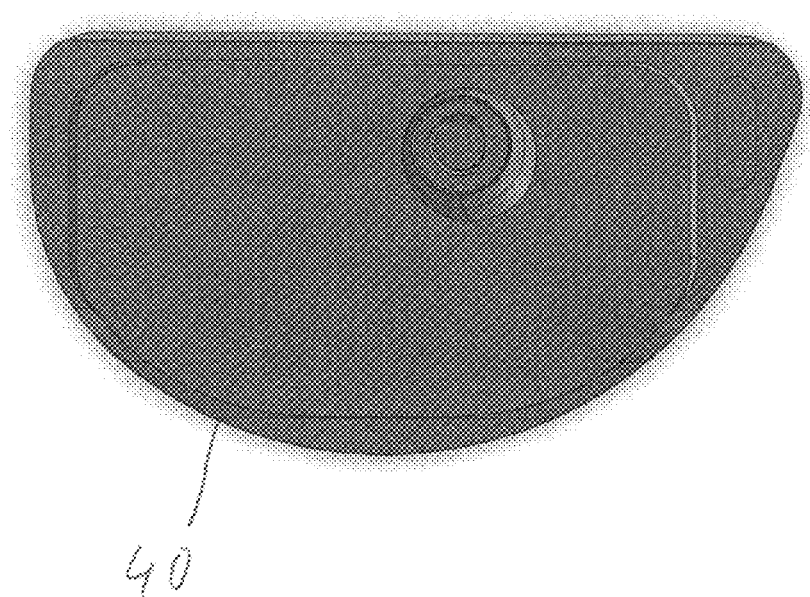
Figure 14:
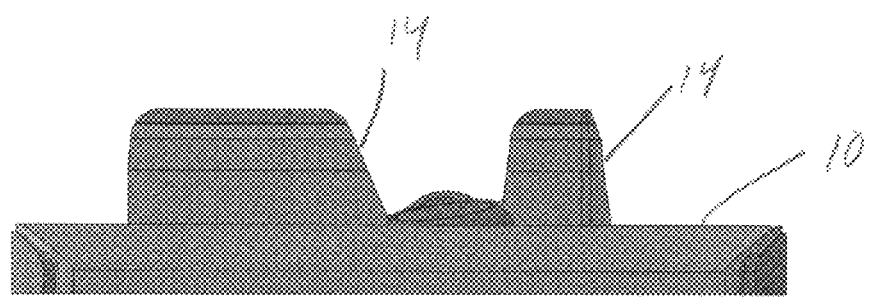
Figure 15:
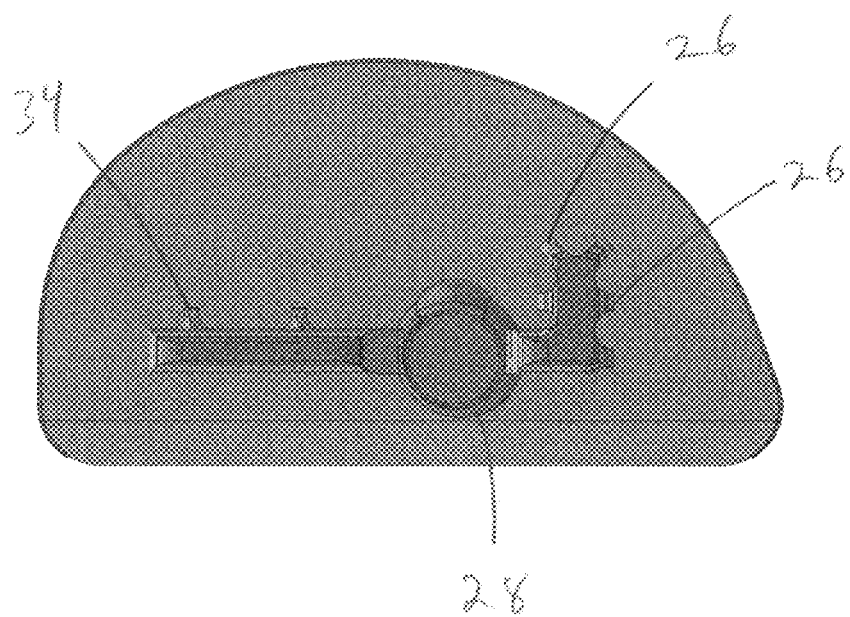
Figure 16:
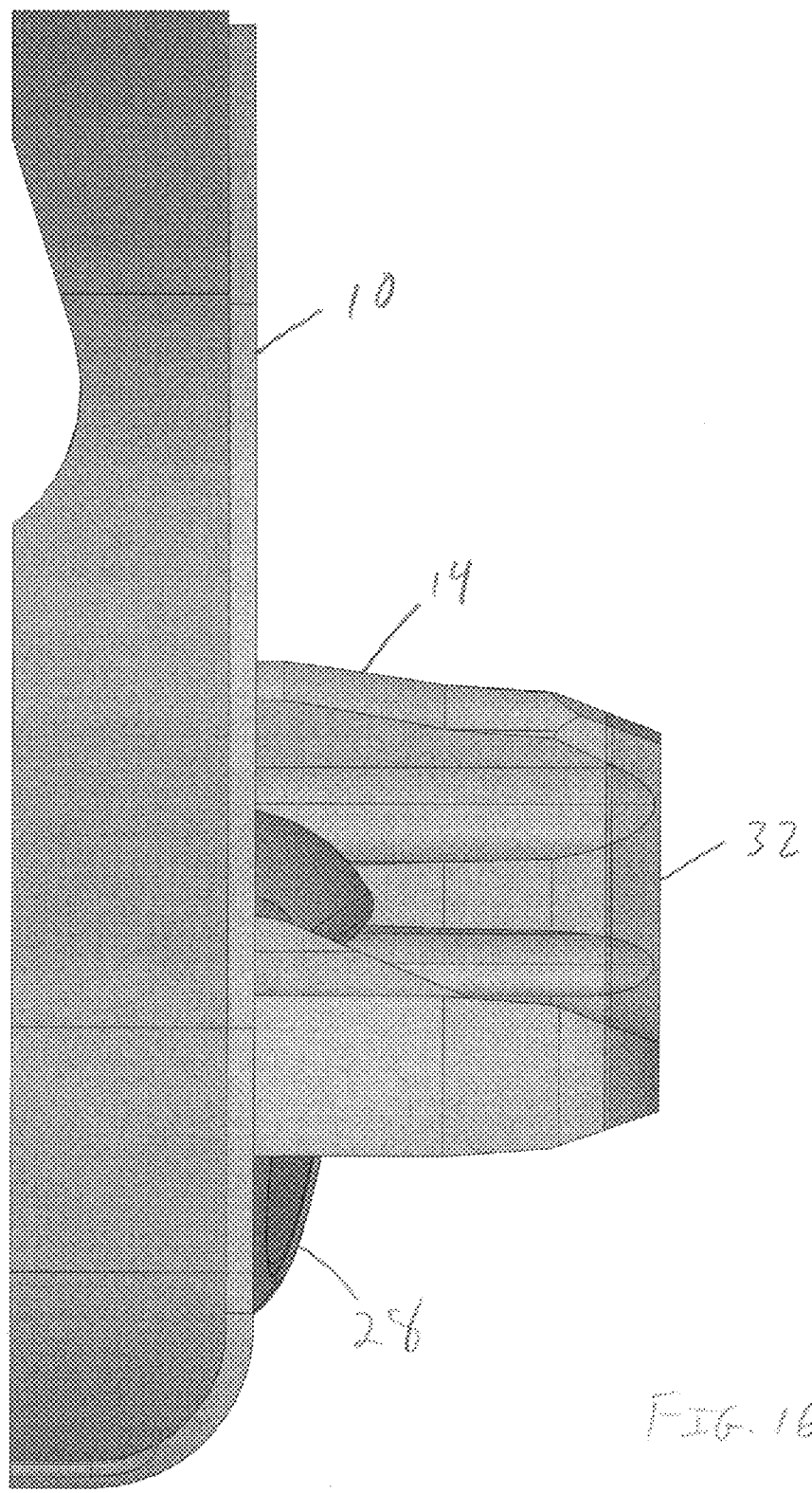
Figure 17:
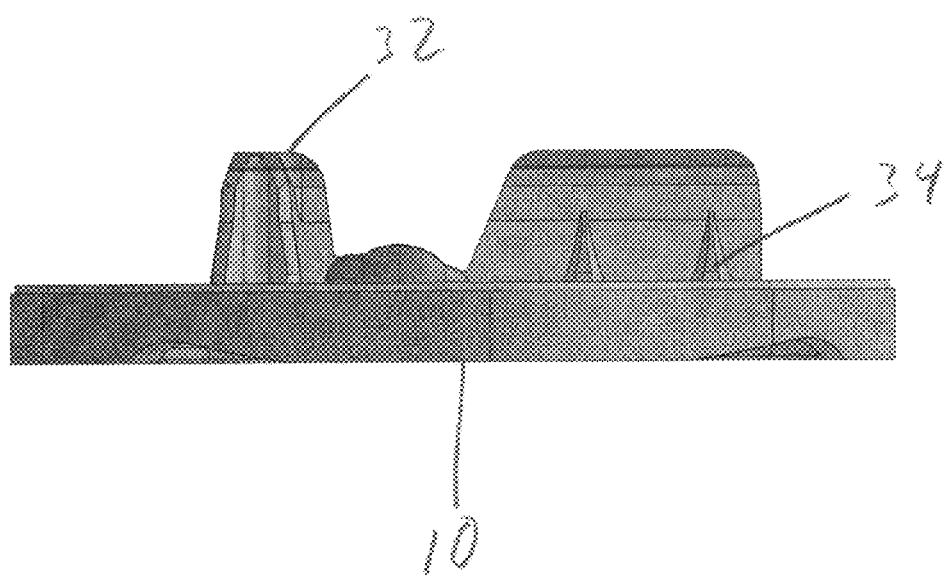
Figure 18:
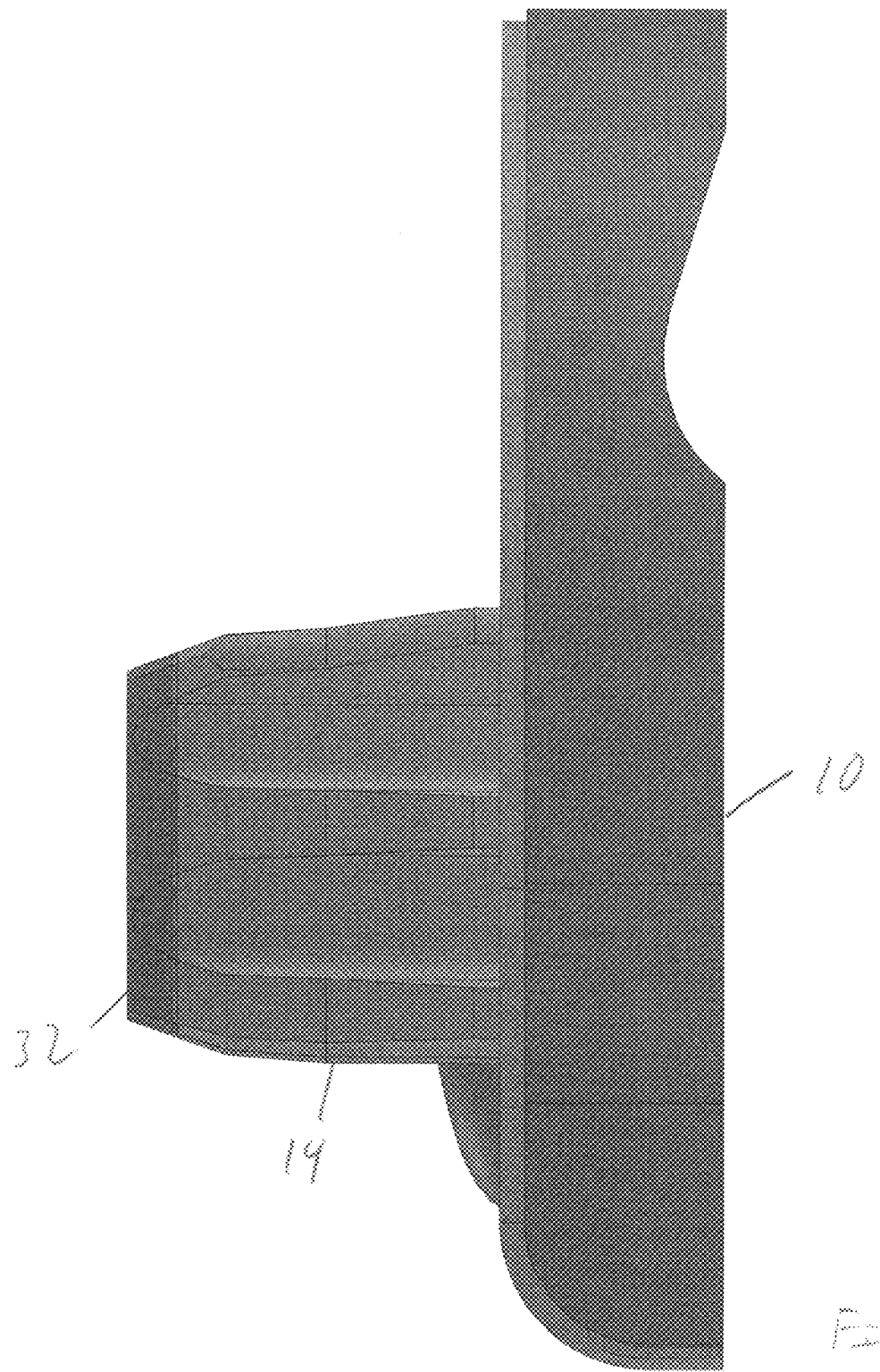

The tibial keel 14 also includes a plurality of fins 34 which extend beyond the nominal volume of the tibial keel 14. The fins 34 enter bone that has not been prepared to receive the fins 34. Instead, the fins 34 prepare their own receiving volume within the bone as they are inserted into the bone, i.e., the fins 34 create their own preparation into the bone. In other words, the fins 34 are inserted into bone without the need to prepare the bone to receive such fins 34. The fins 34 are sized to maximize their surface area, minimize their volume and are shaped to ease entry into the bone. As shown in FIGS. 2 and 7, the fins 34 are preferably configured as shown and are substantially wedge shaped or shaped as a dual inclined plane structure. Further, the fins 34 are tapered as they extend from a proximal end of the tibial keel 14 distally. The fins 34 are also preferably configured to extend an overall length about half way the overall height of the tibial keel 14.

Preferably, the through hole 28 is shaped and sized for the passage of the bone screw 30 (FIGS. 19 and 20) through a superior aspect of the tibial implant 10 into the bone beneath the underside or inferior surface of the tibial tray 18. The bone screw 30 can be angulated to achieve a desired direction by the user. Further, with material from adjacent protrusion 20 removed, the protrusion 20 does not interfere with the passage of the bone screw 30 through the through hole 28. Such bone screws 30 are readily known in the art and a detailed description of their structure and operation is not necessary for a complete understanding of the present invention.

The tibial implant 10 may employ the use of a knockout plug 36 formed within the through hole 28 and out of a material that is metallurgically continuous with the greater bulk of the tibial implant 10. The knockout plug 36 is configured to be removed from the remainder of the tibial implant 10 via a boundary shear section 38 around the plug 36. The plug 36 may be machined into the tibial tray 18 or built in final form through an additive manufacturing process such as by direct metal laser sintering.

Preferably, the through hole 28, designed for the passage of the bone screw 30 therethrough, is obstructed by the knockout plug 36 so that the superior surface 40 of the tibial tray 18 facing the bearing component 12, which can be assembled thereto, is fully continuous without any path through which debris or material could pass through the tibial tray 18 to the bone engaging underside of the tibial implant 10.

In sum, the tibial tray 18 has a through hole 28 into which a screw 30 can be placed to further stabilize the tibial implant 10 to the prepared bone upon implantation. This is especially advantageous for initial implant stability and when placing the tibial implant into bone of questionable density where the user/surgeon is not confident the bone itself is stable enough to support adequate short term stability.

The through hole 28 can be covered during the manufacturing process of the tibial implant 10 with the knockout plug or shear plug 36. The knockout plug 36 has a weak cross section which will yield to an appropriate level of force. When the knockout plug 36 is in place, there exists an uninterrupted tibial tray surface between the poly (i.e., bearing component 12) and the bone interface. In the event of backside wear of the bearing component 12, wear particles are less likely to migrate out of the tibial tray 18 than if an already present through hole were in place. The knockout plug 36 can optionally include a threaded stud 42 (FIG. 12), which mates to instrumentation to facilitate removal of the knockout plug 36.

The porous metal 16 is formed from a porous structured biomaterial, and includes a plurality of struts 44 (FIGS. 21-29) having varying lengths and cross sections. At least one strut of the porous metal 16 has an end connected to one or more other struts at node points 46 (FIG. 29) thereby forming the porous geometry of the porous metal 16. The porous metal 16 also includes boundary struts 48 (FIGS. 26, 27 and 28) that are configured to extend beyond a nominal boundary of the porous metal 16. That is, the porous metal 16 has boundary struts 48 that extend away from the surface of the porous metal 16 in a finger-like or hair follicle-like fashion. The extending boundary struts 48 impart a roughness to the surface, the degree of which is dependent upon the number and length of boundary struts 48 present. The average or main direction of the boundary struts 48 also impart a surface roughness that varies dependent upon which direction the device is driven for implantation.

Preferably, the tibial keel 14 is formed from a metal substrate and a layer of porous metal 16 adjacent the substrate. The porous metal 16 on the tibial keel 14 includes extending boundary struts 48 with unconnected ends pointing or extending towards the bottom or inferior surface of the tibial tray 18. Under similar loading conditions, sliding over the angled struts toward the bottom surface of the tibial tray 18 will experience less frictional forces than bone sliding away from the bottom face of the tibial tray 18. Preferably, the boundary struts 48 are angled about +/−10 degrees from normal to a surface of the substrate to which the porous metal 16 is applied to.

Another element of the present invention is that the boundary struts 48 are oriented in a predetermined direction such that they push or are directed towards the bone interface surface. While the surface of the porous metal 16 may exhibit characteristics of a rougher surface, the boundary struts 48 of the porous metal 16 implanted into a bone interface embed themselves into the bone and provide a mechanical interlock to the surrounding bone. This is especially advantageous during initial implantation for initial fixation purposes. In the aggregate, the plurality of boundary struts 48 significantly improves the overall stability of the tibial implant 10 upon initial implantation.

Preferably, the bottom surface of the tibial tray 18 has extending boundary struts 48' (FIGS. 26 and 27) in a direction substantially normal to the bottom surface of the tibial tray 18. As the tibial implant 10 is definitively seated against the bone interface surface, the boundary struts 48' pierce the surface of the prepared bone to increase stability of the tibial implant 10 to the bone.

The tibial implant 10 has the porous metal 16 on all surfaces that make contact with bone. The surface of the porous metal 16 is tailored for each specific region of the tibial implant 10 to have specific surface roughness and thereby specific amounts of friction when engaged with bone. That is, the tibial implant 10 is configured to have a porous metal 16 with boundary struts 48 at predetermined angles dependent upon the location of the porous metal 16 on the tibial implant 10.

In sum, the surfaces of the porous metal 16 have extending boundary struts 48 which serve to modify the surface roughness of the tibial implant 10. The size and average direction of the extending boundary struts 48 impart different frictional coefficients depending upon the direction the boundary struts 48 extend. The boundary struts 48 can also be directed in a direction largely normal to the surface from which they extend from. This can have an additive anchoring effect which enhances stability of the tibial implant 10 to the bone.

Referring to FIGS. 30-37, in accordance with another preferred embodiment, the present invention provides for a tibial implant 10'. The tibial implant 10' is similarly configured as tibial implant 10, excepted are follows. The tibial implant 10 includes a first protrusion 20' segmented by a void and a second protrusion 22'. The second protrusion 22' is similarly configured as the second protrusion 22 discussed above, but is spaced from the first protrusion 20'. The second protrusion 22' has a height equivalent to the height of the first protrusion 20' adjacent the second protrusion 22'. As best shown in FIGS. 34-36, the height of the first protrusion 20' slopes towards the posterior end of the tibial implant 10' such that the height of the first protrusion decreases as it extends from the anterior end towards the posterior end.

Referring to FIGS. 38-40, the tibial implant 10' can alternatively include a third protrusion 23'. The third protrusion 23', like the second protrusion 22', is slightly spaced apart from the first protrusion 20'. Preferably, the third protrusion 23' is positioned more towards the rear or posterior to the first protrusion and has a height similar to the height of the posterior end of the first protrusion 20' to which it is adjacent to. The height of the third protrusion 23' is not equal to the height of the second protrusion 22' or the height of the first protrusion adjacent the anterior end of the first protrusion 20'. The third protrusion 23' is also configured not to intersect the first protrusion 20'.

Referring to FIGS. 41-43, the third protrusion 23' can also alternatively be positioned toward or about a middle section of the first protrusion 20' and spaced apart from the first protrusion 20'. When positioned about the middle section of the first protrusion 20', the third protrusion 23' has a height substantially the same as the area of the first protrusion 20' that it is adjacent to.

It will be appreciated by those skilled in the art that changes could be made to the embodiments described above without departing from the broad inventive concept thereof. For example, additional components can be added to the tibial implant assembly. It is to be understood, therefore, that this invention is not limited to the particular embodiments disclosed, but it is intended to cover modifications within the spirit and scope of the present invention as described above.

FIGS. 36 and 37 depict yet another embodiment tibial implant 410. Unlike the above-discussed implants, implant 410 includes a keel 414 that is of a unitary design. A hole or aperture 428 is situated offset with respect to the keel 414. This allows for the keel 414 to have a unitary construction (i.e., it is not broken up by the hole 428 as in the above designs). Like the foregoing embodiments, keel 414 includes two projections 420, 422, with the projection 420 including fins 434 and the projection 422 including extensions 426. Of course, as in the above embodiments, either projection could include either or both of the extensions 426 or fins 434, and such structures can be of any shape and or size with respect to the projections. Moreover, keel 414 includes a rounded cut out 421, which allows for a screw 430 to angulate with respect to implant 410. In other words, the cut out 421 provides clearance for the screw 430 to move with respect to the plate in directions towards the keel 414.

It is also to be understood that the disclosure set forth herein includes all possible combinations of the particular features described. For example, where a particular feature is disclosed in the context of a particular aspect, arrangement, configuration, or embodiment, or a particular claim, that feature can also be used, to the extent possible, in combination with and/or in the context of other particular aspects, arrangements, configurations, and embodiments of the invention, and in the invention generally.

Furthermore, although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

The invention claimed is:

1. An orthopedic implant for replacing a portion of a bone comprising:
   a bone contacting surface;
   a hole configured to accept a bone screw at a plurality of different angles; and
   a keel extending from the bone contacting surface, the keel including a first projection with a first longitudinal axis and a second projection with a second longitudinal axis, wherein the first and second longitudinal axes are oriented orthogonally to each other, and the first and second projections are separated from each other by the hole.

2. The orthopedic implant of claim 1, wherein the hole includes a plug removable upon the application of a force.

3. The orthopedic implant of claim 1, further comprising at least one fin associated with the first projection and extending oblique to the first longitudinal axis.

4. The orthopedic implant of claim 3, wherein the fin is shaped to engage the bone.

5. The orthopedic implant of claim 4, wherein the fin is configured to enter into an unprepared portion of the bone.

6. The orthopedic implant of claim 1, further comprising at least one extension associated with the second projection and extending oblique to the second longitudinal axis.

7. The orthopedic implant of claim 6, wherein the at least one extension is shaped to engage the bone.

8. The orthopedic implant of claim 7, wherein the at least one extension frictionally engages the bone.

9. The orthopedic implant of claim 1, further comprising a porous portion adapted to allow for the bone to grow therein.

10. The orthopedic implant of claim 9, wherein the porous portion covers at least a portion of the bone contacting surface and at least a portion of the keel.

11. The orthopedic implant of claim 10, further comprising a solid portion at a distal end of the keel.

12. The orthopedic implant of claim 9, wherein the porous portion defines a first porous surface and at least one boundary strut extending from the surface in a first direction.

13. The orthopedic implant of claim 12, wherein the boundary strut extends from 0 to 10 degrees from normal the first porous surface.

14. The orthopedic implant of claim 1, further comprising a third projection.

15. The orthopedic implant of claim 1, further comprising a bearing component attachable to the implant.

16. The orthopedic implant of claim 1, wherein the implant is a unicondylar tibial baseplate.

17. A kit comprising the implant of claim 1 and at least one other implant.

18. A tibial baseplate comprising:
   a bone contacting surface having anterior, posterior, medial and lateral sides;
   a first projection extending from the bone contacting surface and having a first length extending in a first direction between the anterior and posterior ends;
   a second projection extending from the bone contacting surface and having a second length extending in a second direction between the medial and lateral sides, the second projection being separated from the first projection;
   an aperture for receiving a bone screw; and
   a porous material for promoting bone ingrowth, the porous material at least partially covering the bone contacting surface, the first projection and the second projection, wherein the porous material defines a plurality of boundary struts extending from 0 to 10 degrees from normal to the bone contacting surface.

19. The tibial baseplate of claim 18, further comprising a third projection.

20. The tibial baseplate of claim 18, wherein the first and second projections are separated from each other by the aperture.

21. The tibial baseplate of claim 18, wherein the aperture is configured to accept a bone screw at a plurality of different angles.

22. The tibial baseplate of claim 18, wherein the aperture includes a plug removable upon the application of a force.

23. The tibial baseplate of claim 18, further comprising at least one fin or extension associated with at least one of the first and second projections.

24. The tibial baseplate of claim 23, wherein the fin is configured to enter into an unprepared portion of the bone and the extension frictionally engages the bone.

25. The tibial baseplate of claim 18, further comprising a solid portion at distal ends of the first and second projections.

26. A tibial baseplate comprising:
   a bone contacting surface having anterior, posterior, medial and lateral sides;
   a first projection extending from the bone contacting surface and having a first length extending in a first direction between the anterior and posterior ends;
   a second projection extending from the bone contacting surface and having a second length extending in a second direction between the medial and lateral sides, the second projection being separated from the first projection;
   an aperture for receiving a bone screw;
   a plug at least partially covering the aperture, the plug being removable upon the application of a force; and
   a porous material for promoting bone ingrowth, the porous material at least partially covering the bone contacting surface, the first projection and the second projection, wherein the porous material defines a plurality of boundary struts extending from the bone contacting surface from 0 to 10 degrees from normal to the bone contacting surface.

* * * * *